United States Patent [19]
Benoff

[11] Patent Number: 5,994,086
[45] Date of Patent: Nov. 30, 1999

[54] METHOD FOR ASSESSING INFERTILITY BY BINDING OF MANNOSE TO SPERM CELLS

[75] Inventor: Susan Benoff, Riverdale, N.Y.

[73] Assignee: North Shore University Hospital, Manhasset, N.Y.

[21] Appl. No.: 08/219,690

[22] Filed: Mar. 30, 1994

[51] Int. Cl.[6] .................................................. G01N 33/567
[52] U.S. Cl. .......................... 435/7.21; 435/2.3; 435/29; 436/63; 436/501; 514/8; 514/15; 514/201
[58] Field of Search ................................ 435/23, 7.21, 29, 435/2; 436/63, 501, 906; 514/8, 15, 201

[56] References Cited

PUBLICATIONS

Nardone, P et al, Am. J. Reprod.Immunol.; 1985, vol. 9(4) pp. 124–128.
Silverberg et al, P374, Scientific Abstracts, 1993.
Tesarik et al Jul. 1991, vol. 56(1), pp. 113–118.
Roldan, et al Gamete Research 1986, vol. 13(4), p 281–292.
Nelson et al, Cell Motility, 1982, vol. 2, p 225–242.
Lornage et al, 1983, vol. 10(2), p 119–25, Arch. Androl (USA).
Mortimer et al, 1987, J Rep. Fert. vol. 8; p127–135.
Cross et al; 1986 Gamete Research; 15:213–226; Two Simple Methods for detecting Acrosome–Reacted Human Sperm.
Cross and Overstreet; 1987; Gamete Research 16:23–25 Glycoconjugates of the Human Sperm Surface: Distribution & Alterations that accompany Capacitation In Vitro.
Hong et al; 1984; Br. J. Clin. Pharmac. 17:687–690 Local Anesthetic effect of antiarrythmic drugs and Human Sperm immobilization.
J. Lornage, et al; 1983; Archives of Andrology 10:119–125 Influence of cations & albumin on Human Spermatozoa.
Malmi R. et al; 1987; Andrologia 19(3) 322–332; Distribution of Glycoconjugates in Human testis, A Histochemical Study using Fluorescein–and Rhodamine–conjugated lectins.
Mori, K et al; 1989; Obstet gynecol; 161:207–211 Significance of D–Mannose as a sperm receptor site on the zonapellucida in human fertilization.
Mortimer, D et al; 1987; J. Reprod. Fert. 81, 127–135 Specific labeling by peanut aggtulinin of the outer acrosomal membrane of human spermatozoa.
Nelson, L et al; 1982; Cell Motility 2: 225–242 Regulation of Calcium Distribution in Bovine Sperm cells.
Pandy, V.K. et al; 1983; The Science of the Total Environment 27:49–52;Concentrations of morphologically normal motile spermatozoa: Mg, Ca & Zn in the seman of Infertile men.
Roldan, E.R.S; et al 1986; Gamete Research 13:281–292 Effect of $Ca^{2+}$ Channel Antagonists on the Acrosome Reaction of Guinea Pig and Golden Hamster Sperm.
Silverberg, K.M.; Apr. 3, 1993; Society for Gynecologic Investigation; Abstract #0118, p. 556.
Titeler, M; et al; 1985; J. of Neurochemistry; 44, #6 pp. 1955–1958; [$^3$H]Nitrendipine Binding to Calcium Channels in Bovine and Rat Pituitary.
Benoff et al, abstract O–002, Oct. 13, 1993, Am. Fert. Society, Montreal, Canada.
Benoff et al, Fertility and Sterility, pp. 001–009 Human Sperm–fertilizing potential in vitro is correlated with differential expression of a head–specific mannose–ligand receptor, 1993.

(List continued on next page.)

*Primary Examiner*—James C. Housel
*Assistant Examiner*—Ginny Allen Portner
*Attorney, Agent, or Firm*—Kenyon & Kenyon

[57] ABSTRACT

Methods for labeling mannose lectins on the surface of mammalian sperm cells are described, and methods of categorizing and quantifying the numbers of cells exhibiting particular labeling patterns are also provided. These methods provide ways of detecting whether or not a mammalian male patient has mannose lectin-correlated infertility.

9 Claims, 15 Drawing Sheets

OTHER PUBLICATIONS

Benoff et al., "Demonstration of Homology Between Testis–Specific MAnnose–Acceptor–A Putative Zona Recognition Lectin and the Human Macrophage Mannose–Receptor Lectin", *Abstracts of the Scientific Oral and Poster Sessions*, The American Fertility Society, p. S12, (1992).

Benoff et al., "Antisperm Antibodies Block Mannose–Acceptor Lectin Expression on Fresh and Capacitated Human Spermatozoa", *Abstracts of the Scientific Oral and Poster Sessions*, The American Fertility Society, pp. S17–S18, (1992).

Benoff et al., "Human Sperm Fertilizing Potential in IVF is Correlated With a Mannose–Specific Lectin Whose Surface Expression is Dependent on Membrane Cholesterol Loss", *Abstracts of the Scientific Oral and Poster Sessions*, The American Fertility Society, pp. S165–S166, (1992).

Benoff et al., "Investigations into the Structure of a Putative Zona Recognition Molecule on the Surface of Capacitated Human Sperm–A Mannose–Receptor Lectin", *Society for Gynecologic Investigation*, p.178, (1993).

Benoff et al., "Antisperm Antibodies Interfere with Human Sperm Mannose Receptor Binding", *Society for Gynecologic Investigation*, p.283, (1992).

Benoff et al., "Cholesterol Affects Surface Expression of Human Sperm Mannose Receptors", *Society for Gynecologic Investigation*, p.186, (1992).

Benoff et al., "Sperm Surface Mannose–Specific Lectin: A Molecular Marker for Capacitation Events", *Society for Gynecologic Investigation*, p.326, (1992).

Benoff et al., "Human Sperm Surface Putative Zona Recognition Molecules are Mannose–Receptor Lectins", *American Society of Andrology*, p.24 (1993).

Benoff et al., "The Effect of Calcium Ion Channel Blockers on Sperm Fertilization Potential", *Abstracts of the Scientific Oral and Poster Sessions*, The American Fertility Society, pp.S1–S2, (1993).

Gilbert et al., "Absence of the Human Sperm Membrane Zona Acceptor and Acrosome Reaction in Subfertile Men With Varicoceles", *Abstracts of the Scientific Oral and Poster Sessions*, The American Fertility Society, p. S78, (1993).

Benoff et al., "Progesterone Receptor Surface Expression on the Plasma Membrane of Human Spermatozoa", *Abstracts of the Scientific Oral and Poster Sessions*, The American Fertility Society, pp. S195–196, (1993).

Benoff et al., "Effects of Varicocele Ligation on Parameters of Sperm Fertilizing Potential: Mannose Lectin Expression and Acrosome Status", *Society for Gynecologic Investigation*, p.140, (1994).

Benoff et al., "Calcium Antagonists: Model for Reversible Inhibition of Sperm Fertilizing Potential", *Society for Gynecologic Investigation*, p. 249, (1994).

Benoff et al., "Effects of Xenobiotics on Surface Expression of Mannose–Binding Lectins and Acrosome Status", *Society for Gynecologic Investigation*, p. 249, (1994).

Florman et al., "Activation of Voltage–Dependent Calcium Channels of Mammalian Sperm Is Required for Zona Pellucida–Induced Acrosomal Exocytosis", *Society for Gynecologic Investigation*, p. 249, (1994) Developmental Biology, vol. 152, pp.304–314, (1992).

FIG. 1

Mannosylated Polyacrylamide Bead Binding Studies
(Repeated Tests With An Individual Fertile Sperm Donor)

| Specimen | Average Percentage (Range) | | | | |
|---|---|---|---|---|---|
| | Head | MP* | TT | No Binding | |
| Untreated sperm:<br>0 Time - Swim-up 1 hour at 37 degrees C into BWW | 3.6<br>(2-5) | 2<br>(0-5) | 7.4<br>(2-10) | 90.8<br>(89-93) | |
| 0 Time - Quench: 20 mM mannose + MPBs | 0.25<br>(0-1) | — | 1.75<br>(0-3) | 98.0<br>(97-100) | |
| 0 Time - Quench: 20 mM galactose + MPBs | 2.5<br>(2-3) | — | 2.5<br>(2-3) | 95.5<br>(95-96) | |
| Incubated sperm:<br>18 hours at RT in 5 mg/mL BSA | 36.6<br>(30-44) | 2.2<br>(0-4) | 8.8<br>(6-14) | 58<br>(50-65) | |
| 18 hours at RT in 5 mg/mL BSA -<br>Quench: 20 mM mannose + MPBs | 4.3<br>(2-8) | — | 0.75<br>(0-1) | 95.3<br>(92-98) | |
| 18 hours at RT in 5 mg/mL BSA -<br>Quench: 20 mM galactose + MPBs | 32.5<br>(31-34) | 1<br>(0-2) | 3<br>(2-4) | 64<br>(62-65) | |

*MP - midpiece; TT - tail tip; BWW - Biggers, Whitten and Whittingham medium; MPBs - mannosylated polyacrylamide beads; RT - room temperature; BSA - bovine serum albumin

_5,994,086_

METHOD FOR ASSESSING INFERTILITY BY BINDING OF MANNOSE TO SPERM CELLS

FIELD OF THE INVENTION

This invention relates to a method for determining the distribution of mannose lectins on the surface of mammalian sperm cells. More specifically, this invention relates to a method of quantitating the distribution of mannose lectins on mammalian sperm cells wherein the relative number of sperm cells that are labeled in distinctive patterns on their surfaces is determined. In addition, this invention relates to a method for detecting whether or not a mammalian male patient has mannose lectin-correlated infertility, which is determined on the basis of the relative numbers of sperm cells labeled with particular labeling patterns.

This invention further relates to a method for detecting capacitation-induced changes in the distribution of mannose lectins on mammalian sperm cells. It also relates to a method for detecting whether or not a mammalian male patient has mannose lectin-correlated infertility, wherein the relative percentage of cells having particular mannose lectin labeling patterns both before and after capacitation is determined, and the comparative relative labeling in said capacitated and non-capacitated sperm cells is used as a means of determining fertility or infertility.

This invention also relates to a kit for determining the distribution of mannose lectins on mammalian sperm cells, and also to a method of screening candidate compounds for possible effects on mammalian sperm cell mannose lectin distribution and fertility.

BACKGROUND OF THE INVENTION

1. Clinically Used Methods for Detecting Sperm Fertility Problems

The incidence of male infertility in couples desiring conception has been estimated to be as great as 15% to 40% (11). Despite the great strides that have been made in understanding and treating infertility, one of the greatest difficulties has been the lack of adequate means to diagnose the existence, and potentially the cause, of the male contribution to such infertility.

Methods for evaluating male infertility are currently limited to the assessment of a few general aspects of function (7,8) and these largely depend upon determining whether the sperm meets certain descriptive criteria. The most commonly relied-upon "classical" parameters of semen analysis are sperm number, motility and morphology, and ability to penetrate the cervical mucus (14). Unfortunately, when such parameters are analyzed by different laboratories, there are substantial variations in the results obtained (12,18,19). In addition, if samples of the same patient are tested repeatedly, the results can be substantially different, and the results can also vary considerably when tests from multiple samples of known fertile sperm are compared (20,21).

Even though such analysis has its problems, human male infertility can often be correlated with specific derangements in sperm characteristics. However, there is a subset of infertile men who have normal sperm parameters, yet repeatedly fail to fertilize oocytes in vitro. The lack of a method to detect such infertility leads to much frustration and expense, as such patients can only learn about it by repeated failures in efforts to undergo in vitro fertilization (IVF).

The need to find a more reliable indicator of male infertility has been a long-felt one, and has even encouraged some to evaluate the use of extremely complex methods of analysis. For example, some investigators have attempted to measure sperm movement characteristics using computerized systems that can reconstruct how sperm move (reviewed in Ref. 8). Investigators have also tried to apply an animal model that examines the motility of hyper-activated sperm as an indicator of fertilizing ability (1). Unfortunately, no more than 24% of all human spermatozoa incubated 3 to 24 hours conform to this animal model (22).

That even sophisticated methods of observing sperm numbers or mobility do not yield suitable tests for sperm fertility is not all that surprising, since more than 80% of infertile males have sperm counts which meet or exceed the "normal standards" (20), and since fertility only requires that a small fraction of sperm be functional (22,23). Observations of the sperm as a group is therefore not likely to be accurate.

2. Cellular Events Leading to Fertilization

Efforts to understand the process of fertilization has led to the possibility that distinct molecular markers might be evaluated to determine if sperm can undergo the fertilization process properly.

Before fertilization can occur, human sperm must undergo a special pre-conditioning series of maturation steps that together are known as "capacitation"; only then can they recognize and fertilize human eggs (reviewed in 26). The stages of a sperm cell's capacitation are:

1. The sperm cell develops a vigorous nonlinear flagellar motility, which is known as "hyper-activation";
2. The sperm cell then binds to the proteinaceous layer surrounding the egg (the zona pellucida), in a species-specific manner;
3. The sperm cell then ejects from the head portion, by the process of exocytosis, certain materials that have been accumulated into the head of the sperm into a region called the "acrosome" (this exocytosis of the acrosome is called the "acrosome reaction"); and finally,
4. The sperm fuses with the oolemma and fertilizes the egg.

Although the process of capacitation is understood morphologically, the ultrastructural and biochemical changes that are involved are only beginning to be understood (1). For example, in animals, it has been demonstrated that the expression of sperm membrane proteins which recognize specific glycoconjugates on the zona is altered during capacitation (reviewed in Ref. 2), and that interaction of these sperm proteins with zona ligands triggers the acrosome reaction (3,4). There is fragmentary evidence suggesting that analogous processes occur in man (5–7). However, no study has conclusively established the molecular nature of human sperm zona binding proteins, nor has there been a demonstration of the time course of appearance on the sperm surface of putative zona receptors.

3. Theoretical Foundation for the Invention

The basis for this invention is the hope that if sperm membrane proteins involved in capacitation could be identified and characterized, it might be possible to establish criteria that would distinguish the identity and character of such proteins in normal, fertile cells as opposed to infertile sperm cells. Such a method might also provide a better understanding of biochemical abnormalities involved in human sperm dysfunction, a subject of increasing interest to many clinicians (8,9).

Unfortunately, research directed at identifying and characterizing proteins on the human sperm surface that mediate capacitation in general, and the zona penetration step in particular, have suffered from the limited availability of human oocytes. Recently, however, Mori and co-workers examined the role of monosaccharides in human fertilization (10). Utilizing sugar competition in human sperm-zona binding/penetration experiments, they identified mannose as a saccharide critical for human zona recognition. Sperm binding and penetration occurred when zonae pellucidae were pre-treated with D-mannose. In contrast, when human oocytes were pre-treated with Concanavalin A, a mannose-binding lectin, no human sperm bound to or penetrated the zona. Pretreatment of sperm and co-incubation of sperm and zonae with D-mannose markedly reduced zona binding and completely inhibited zona penetration. The inhibition of sperm binding by D-mannose pretreatment was considerably stronger than that observed with any other monosaccharide or complex sugar tested.

4. Prior Methods Using Mannose Lectin Labeling

Other investigators have attempted to apply these observations to the study of male infertility, but their results have not been clinically useful. In one such effort, Tesarik and co-workers (7) attempted to surface label sperm with bovine serum albumin (BSA) that had been coated with mannose and labeled with a fluorescent tag, fluorescein isothiocyanate (FITC), in order to distinguish fertile from infertile males. Upon observing sperm samples labeled in this way, Tesarik et al. counted individual sperm as falling into three basic groups: (1), head and tail labeled; (2) tail only; or (3) head only (or only part of the head labeled, (3A)). However, Tesarik et al. reported that the overall incidence of labeling was low (only 10–15% bound the probe), and that virtually all sperm showing any of these labeling patterns (or any labeling at all) were acrosomal intact, i.e., they had not undergone the acrosomal reaction.

Based upon analysis of pooled sperm samples from fertile and infertile donor groups, Tesarik et al. also found that about 5.5% of the sperm in fertile samples were labeled only in the head (patterns 3 or 3A), while only about 1.5% of the infertile samples had such binding. Even though this was by their analysis statistically significant, these differences are too slight to be of practical utility, and this method did not meet with widespread clinical use.

In another report, Silverberg and colleagues (27,28) labeled the mannose lectin present in "swim-up" sperm samples (i.e., selected for active motility, see methods below). This was done by incubating the samples with FITC-labeled mannosylated BSA, and then washing to remove the unbound label. Sperm samples were then examined under a microscope, and were characterized as to the percentage of sperm cells that were labeled. Oddly, they refer to Tesarik et al. to say how binding was assessed, but they then did not appear to segregate binding patterns, but only state the total percentage of sperm that were labeled.

Silverberg et al.'s findings were that patients whose sperm cells were zero to 34% labeled had about a 25% chance of succeeding in in vitro fertilization (IVF); that patients whose sperm cells were 35–49% labeled had about a 69% chance of successful IVF; and that those with 50–100% of their sperm cells labeled had about an 82% chance of successful IVF. However, these findings are difficult, if not impossible, to use as a predictive test of whether an individual patient is a good candidate for IVF. There is no indication in these reports regarding the fertilization rate they generally achieved with IVF even with fertile men, or what their insemination criteria were. Furthermore, it is difficult to imagine that someone whose sperm are labeled at 30%, for example, would decline IVF on that basis; even with marginally fertile men, it is often possible to still obtain fertilization if large numbers of sperm are used.

Advantages and Summary of the Invention

The prior art methods described above do not meet the clinical need for a simple, fast and accurate means of detecting and measuring mannose lectin locations on sperm cell surfaces, which would be useful for detecting infertility generally. The prior art methods also do not provide a means of detecting types of infertility that cannot be detected by observation of the widely-used functional parameters.

It is one object of the invention, then, to provide a method for determining the distribution of mannose lectins on the surface of mammalian sperm cells. More specifically, it is an object of the invention to provide a clinically useful means of testing sperm samples to determine fertility or infertility.

Another object of the invention is to provide a mannose lectin labeling method in which background label binding is substantially reduced.

It is another object of the invention to provide a method for quantitating the distribution of mannose lectins on mammalian sperm cells wherein the relative numbers of sperm cells that are labeled in distinctive patterns on their surfaces are determined.

It is another object of this invention to provide a method for detecting whether or not a mammalian male patient has mannose lectin-correlated infertility, which is determined on the basis of the relative numbers of sperm cells labeled with labeling particular patterns.

A further object of this invention is to provide a method for detecting capacitation-induced changes in the distribution of mannose lectins on mammalian sperm cells.

It is also an object of this invention to provide a method for detecting whether or not a mammalian male patient has mannose lectin-correlated infertility, wherein the relative percentage of cells having particular mannose lectin labeling patterns both before and after capacitation is determined, and a comparison of the relative labeling in said capacitated and non-capacitated sperm cells is used as a means of determining such fertility or infertility.

It is a further object of this invention to provide a kit for determining the distribution of mannose lectins on mammalian sperm cells.

It is also an object of this invention to provide a method of screening candidate compounds for possible effects on mammalian sperm cell mannose lectin distribution and on fertility.

The present invention takes advantage of new information regarding the movement of mannose lectins on the surface of sperm cell membranes, but does so with a number of important differences from the approaches used in the prior art.

In one embodiment of the invention, a method is used that takes advantage of the finding that adding calcium to the labeling medium appears to greatly aid in the binding of the cells to the mannose-conjugated label. In addition, the calcium content of the wash medium is lowered below that of the labeling medium in order to prevent non-specific label binding.

In another embodiment of the invention, sperm cells are examined to determine the relative numbers that are labeled according to labeling patterns I, II and III, as hereinbelow defined. In this embodiment, cells are examined for the presence of distinct and substantially different labeling patterns than those described in the prior art. Furthermore, contrary to the teachings of the prior art, in this embodiment, mannose lectin labeling patterns are observed in acrosome-reacted sperm as well as acrosome-intact sperm. In a related embodiment, the relative numbers of cells binding in said patterns is used as an indicator of fertility or infertility.

In yet another embodiment, cells are pre-incubated in a capacitation medium preferably containing a protein, e.g.

serum albumin, which pre-incubation gives an improved ability to distinguish fertile and infertile sperm samples. In a related embodiment, comparing the numbers of sperm cells having pattern II labeling before and after capacitation is used as a means of detecting fertility or infertility.

Several of the foregoing embodiments are clinically useful as fertility tests. Their clinical utility derives from their unique differences from the prior art methods: different ligand, labeling and capacitation conditions; the ability to detect mannose-binding lectin on acrosome-reacted sperm; and in patient selection and mode of specimen analysis (for example, Tesarik et al. (7) apparently pooled specimens from different fertile or infertile males, whereas in the preferred embodiments of this invention, sperm specimens from each male are individually processed). Furthermore, the present invention provides incremental increases in mannose lectin labeling for the fertile group in comparison to the infertile group that are considerably larger than the prior art methods provide.

In additional embodiments, the methods of the present invention are used to determine if drugs, drug candidates, toxins or environmental pollutants, which compounds are administered to sperm cells in vitro or ingested by patients in vivo, have an impact on sperm cell mannose lectin distribution and/or a positive or negative impact on male fertility. These embodiments are of value in screening environmental hazards for fertility effects in men, and to test whether particular drugs or drug candidates might be useful as male contraceptives, or as agents that can be used to treat male infertility.

The appended claims are hereby incorporated by reference as an enumeration of the preferred embodiments.

BRIEF DESCRIPTION OF THE DRAWINGS

FIG. 1 shows summarized data from mannosylated polyacrylamide bead binding studies, indicating the average percentages of head, midpiece, and tail tip binding for untreated and incubated sperm, both with and without quenching by added mannose.

3(A) The three distinct Man-FITC-neoglycoprotein ligand surface labeling patterns which exist on sperm are represented in the photomicrograph. The small arrow is pointing to the non-specific labeling of the neck/midpiece region (I=pattern I) seen on all sperm. The large arrow indicates head-directed uniformly distributed surface labeling occurring with different intensities over the acrosome and post-acrosomal regions (II=pattern II). The open arrowhead points to the intense equatorial/post-acrosomal band (III=pattern III) observed only in acrosome-reacted sperm.

(B) Examination of the corresponding RITC-PSA labeling patterns of Man-FITC-neoglycoprotein ligand labeled sperm shown in Part A demonstrates that pattern II sperm are acrosome intact whereas pattern III sperm have undergone an acrosome reaction. Note the uniform and intense label on intact acrosome of pattern II sperm (large arrow) as well as the overall diminished fluorescence intensity of the acrosomal cap with increased fluorescence in the equatorial region characteristic of acrosome-reacted sperm (open arrowhead).

Figure 4:
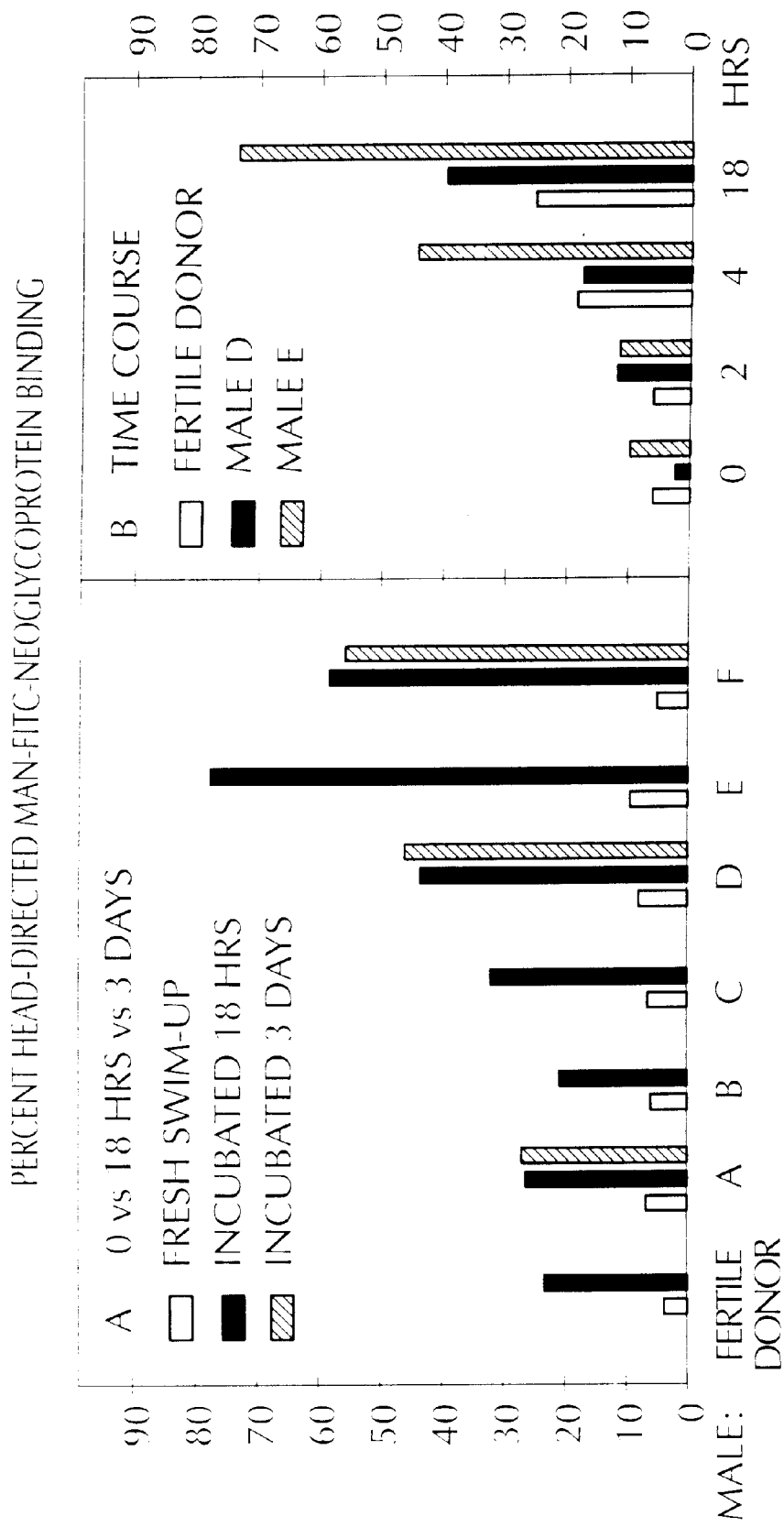

FIG. 4. shows the relationship between expression of surface D-mannose binding sites and incubation in capacitating medium. The bars in the figure represent the total combined percentage of Man-FITC-neoglycoprotein surface labeling patterns II and III ("head-directed labeling") in each preparation and are typical results obtained by analysis of specimens from a donor of known fertility (Fertile Donor; see FIG. 1) and males A–F chosen at random from semen presenting for routine analysis. FIG.4(A) is a comparison of untreated and plateau (18 hour) values; FIG.4(B) shows the time course of surface expression for Fertile Donor and males D and E.

Figure 5:
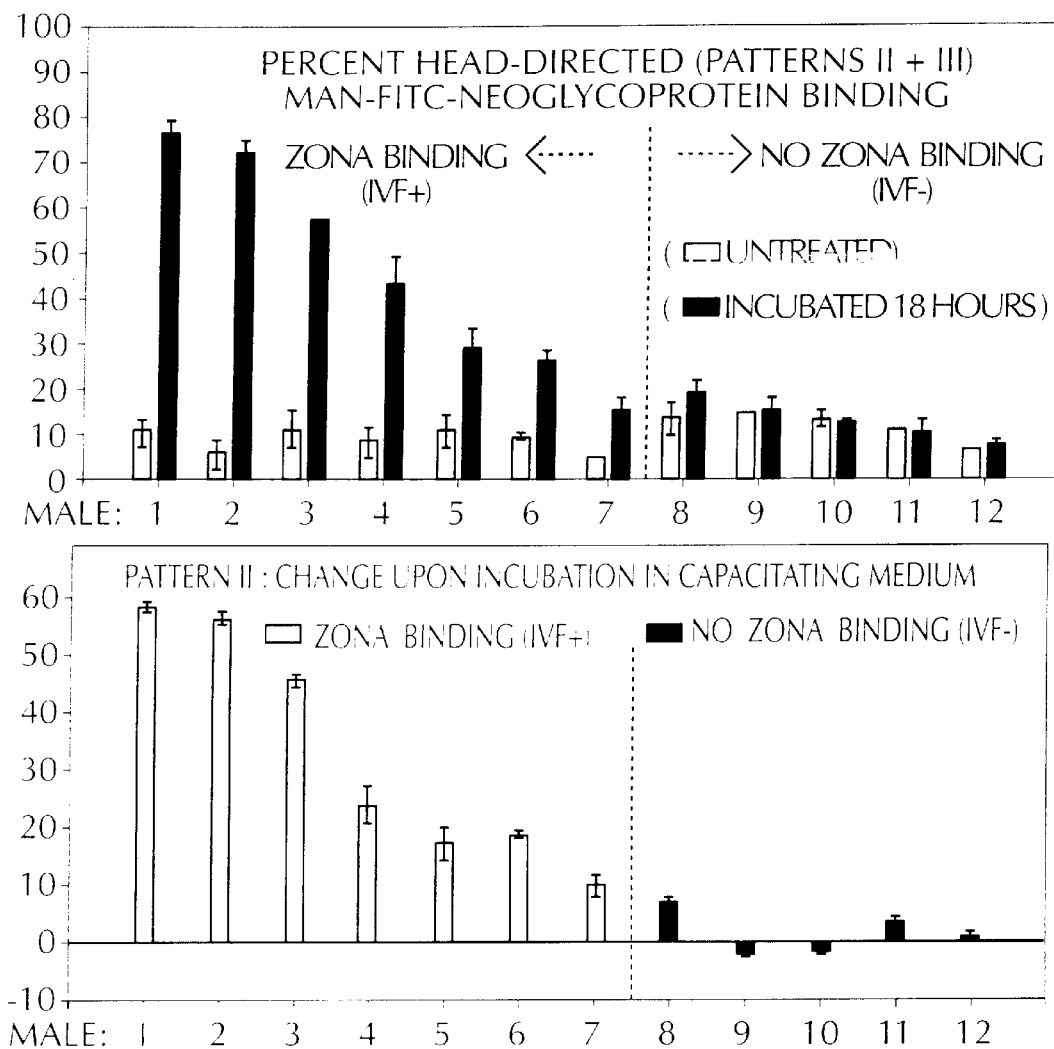

FIG. 5 shows the results of a retrospective double blind analysis of the mannose ligand binding characteristics of fresh and/or liquid nitrogen frozen/thawed-Percoll gradient purified semen from patients in an in vitro fertilization program. The bars represent the mean values (with one standard error of the mean indicated [I]), obtained by analysis of at least 3 independent specimens from each male undergoing IVF treatment, as evaluated by two independent observers.

5(A) shows the percentage of sperm in each preparation exhibiting head-directed patterns (II and III) following incubation for 16–20 hours in medium supplemented with 30 mg/mL HSA, as determined by visual inspection;

(B) shows the percentages of sperm exhibiting pattern II in fresh specimens and in duplicate aliquots exposed to capacitating medium.

The bars in the figure represent the net difference in pattern II labeling between capacitated and fresh, untreated specimens.

FIGS. 6–10 show the results of experiments that illustrate the utility of the method in detecting and characterizing the effects of toxic metals on sperm mannose lectins and fertility.

Figure 9:
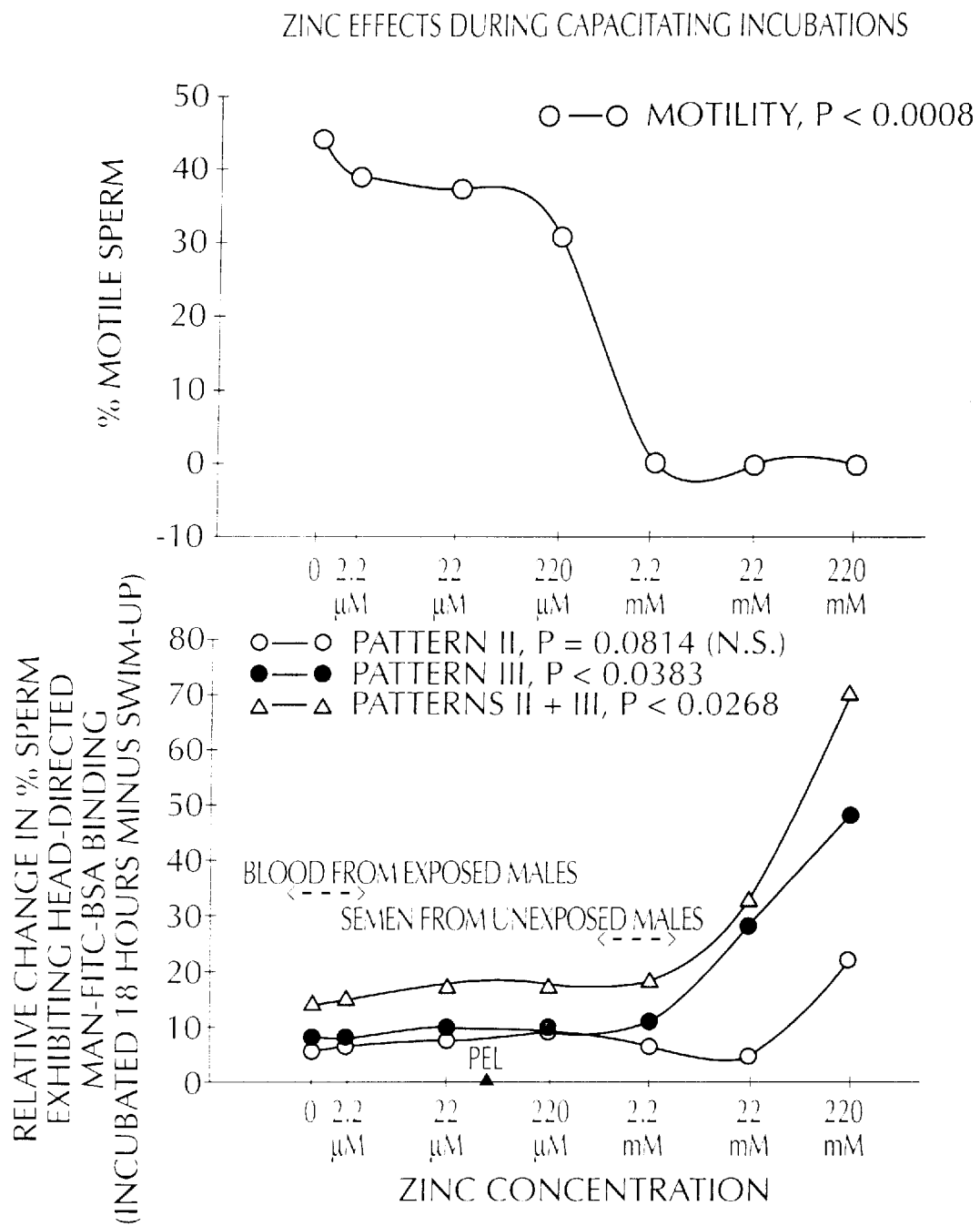
Figure 10:
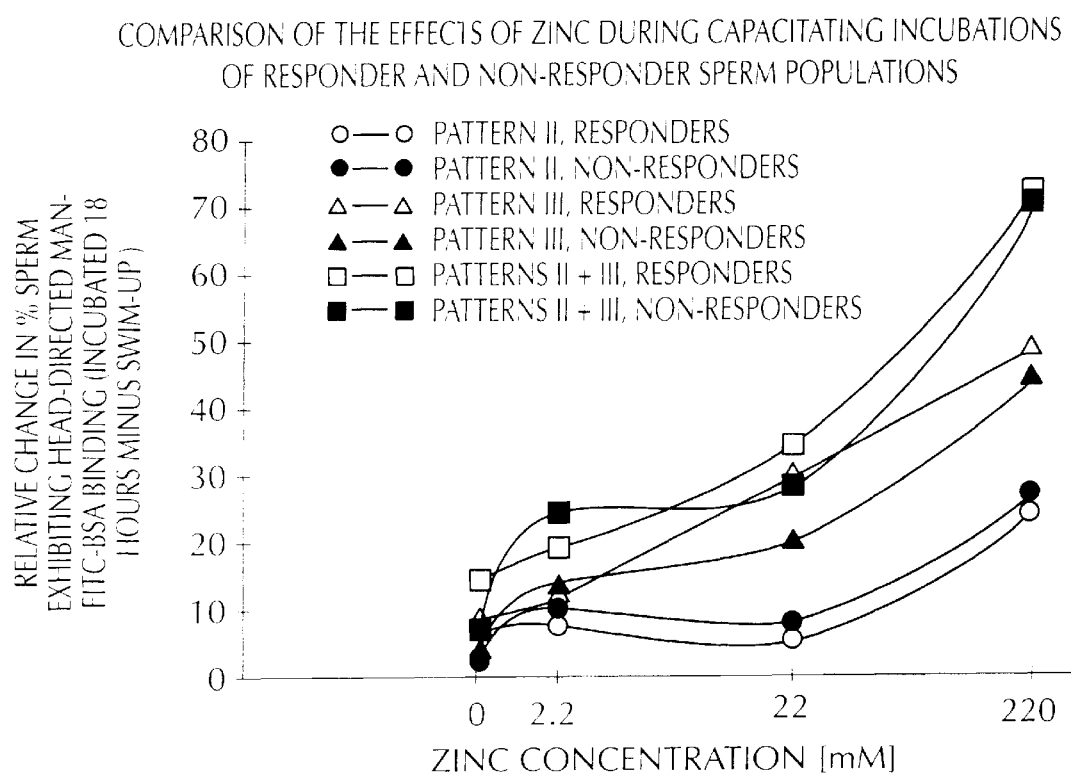

FIGS. 6A & B, FIG. 6A shows the relative change in the percent of motile sperm and FIG. 6B shows the percent of sperm exhibiting head-directed mannose lectin labeling in the presence of increasing concentrations of cadmium;

FIGS. 7A & B, FIG. 7A shows the relative change in the percent of motile sperm and FIG. 7B shows the percent of sperm exhibiting head-directed mannose lectin labeling in the presence of increasing concentrations of manganese;

FIGS. 8A & B, FIG. 8A shows the relative change in the percent of motile sperm and FIG. 8B shows percent of sperm exhibiting head-directed mannose lectin labeling in the presence of increasing concentrations of nickel;

FIGS. 9A & B, FIG. 9A shows the relative change in the percent of motile sperm and FIG. 9B shows percent of sperm exhibiting head-directed mannose lectin labeling in the presence of increasing concentrations of zinc; and FIG. 10 shows the relative change in the percent of motile sperm and the percent of sperm exhibiting head-directed mannose lectin labeling in the presence of increasing concentrations of zinc when sperm from IVF-infertile non-responders and normal responders are tested side-by-side.

Figure 11:
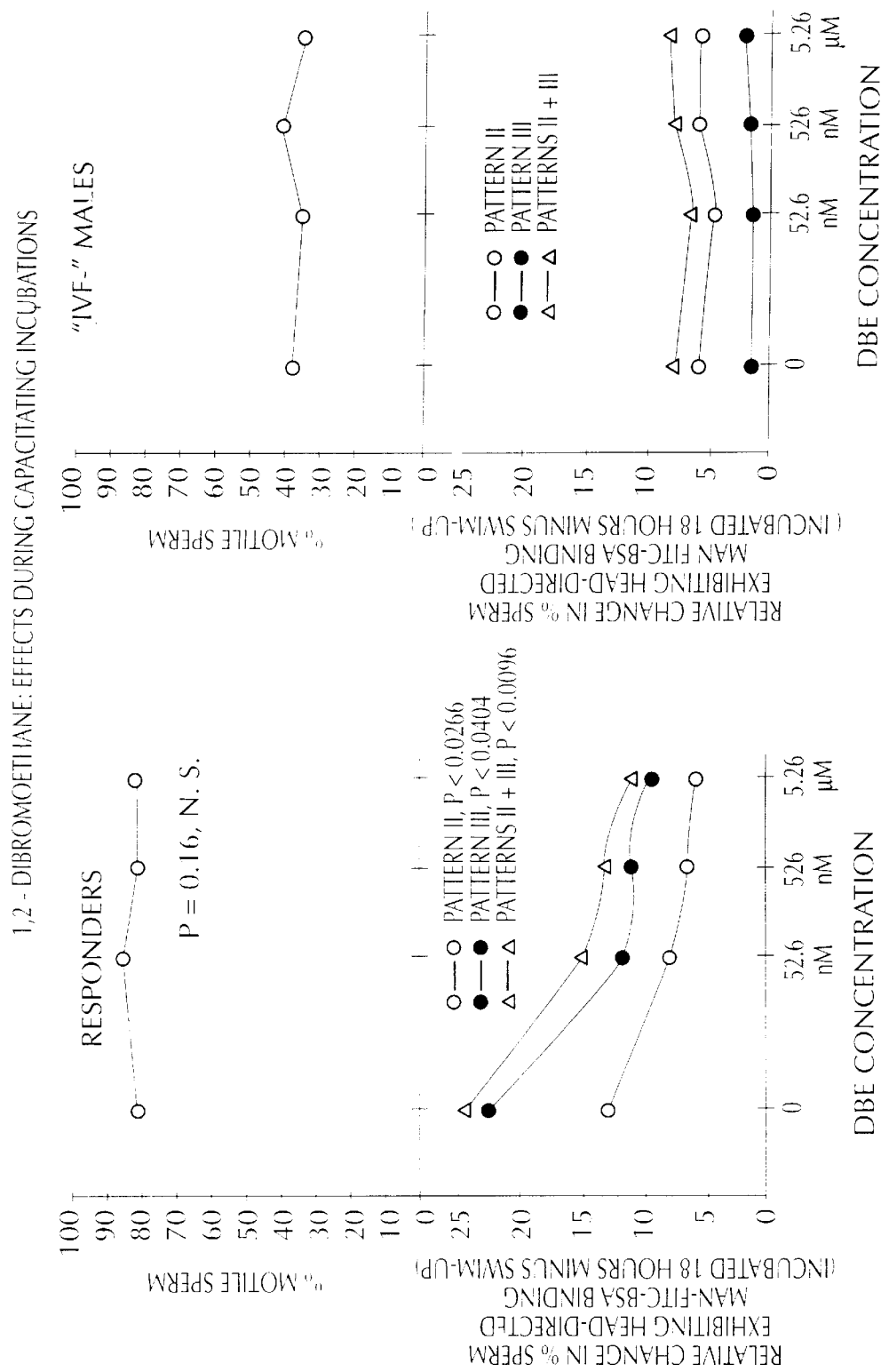
Figure 12:
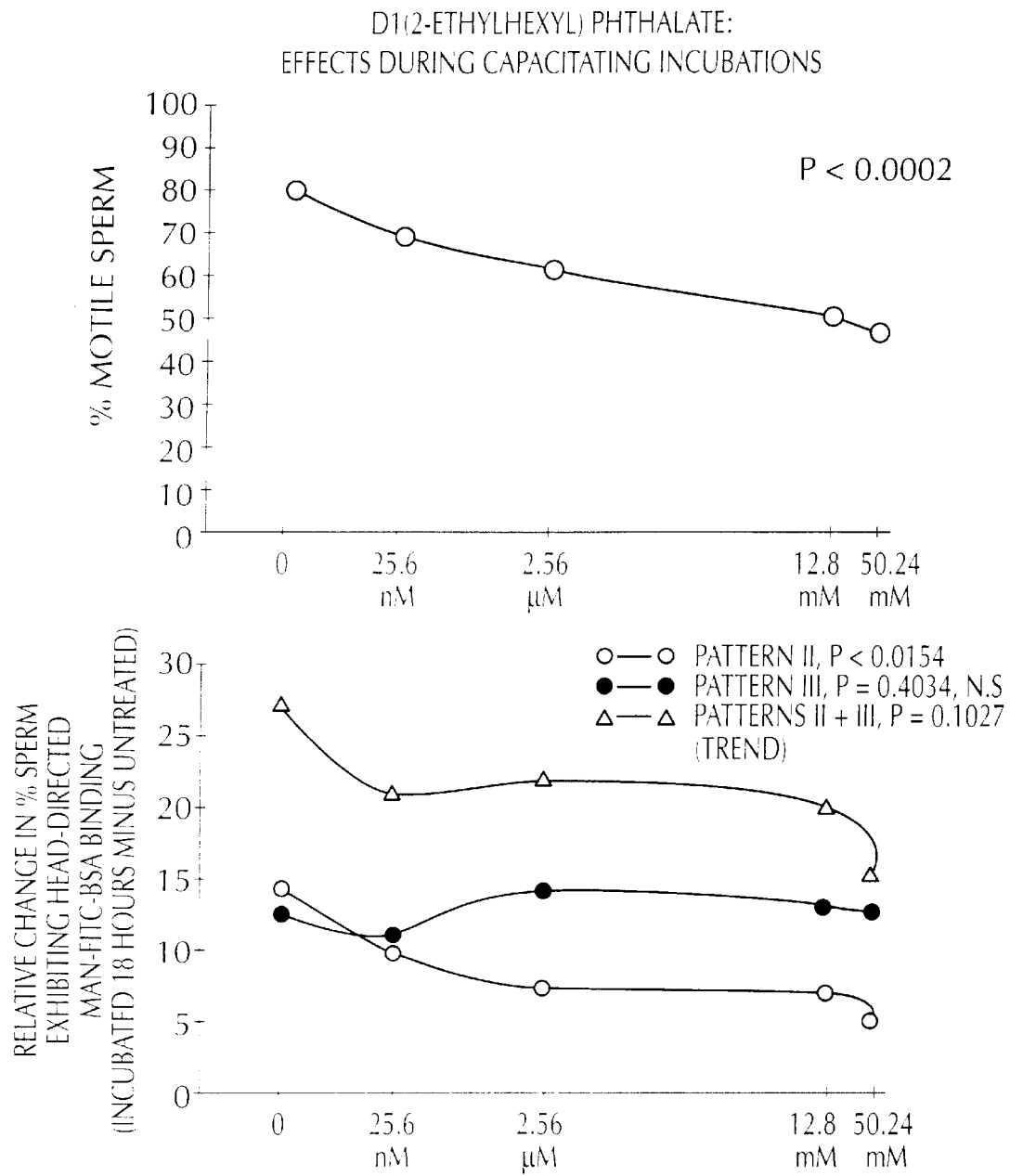
Figure 13:
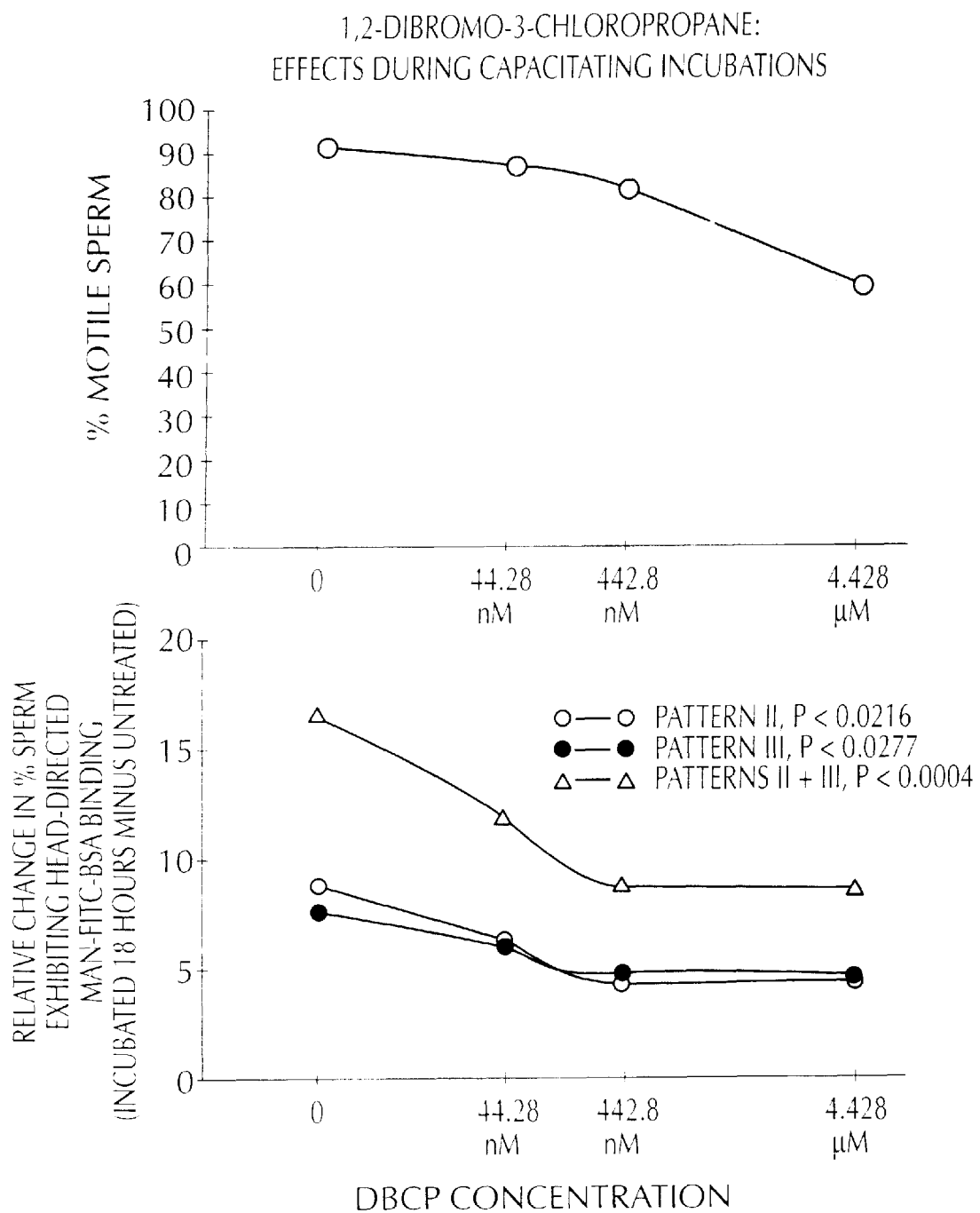

FIGS. 11–13 illustrate the value of the method in assessing the effects of toxic organic compounds on mannose lectin labeling and fertility.

FIGS. 11A–D, FIG. 11A–B shows the relative change in the percent of motile sperm FIG. 11, C–D shows and the percent of sperm exhibiting head-directed mannose lectin labeling in the presence of increasing concentrations of 2,2-dibromoethane;

FIGS. 12A & B, FIG. 12A shows the relative change in the percent of motile sperm FIG. 12B shows and the percent of sperm exhibiting head-directed mannose lectin labeling in the presence of increasing concentrations of phthalate ester;

FIGS. 13A & B, FIG. 13A shows the relative change in the percent of motile sperm FIG. 13B shows and the percent of sperm exhibiting head-directed mannose lectin labeling in the presence of increasing concentrations of 1,2 dibromo-3-chloropropane.

FIGS. 14A–C, FIG. 14A shows the relative number of cells with head-directed mannose lectin labeling, FIG. 14B–C shows sperm cells both before and after capacitation in sperm samples from patients being treated with calcium channel blocking drugs (nifedipine or verapamil), in comparison with fertile sperm or sperm from patients taking other anti-hypertensive medications.

Figure 15:
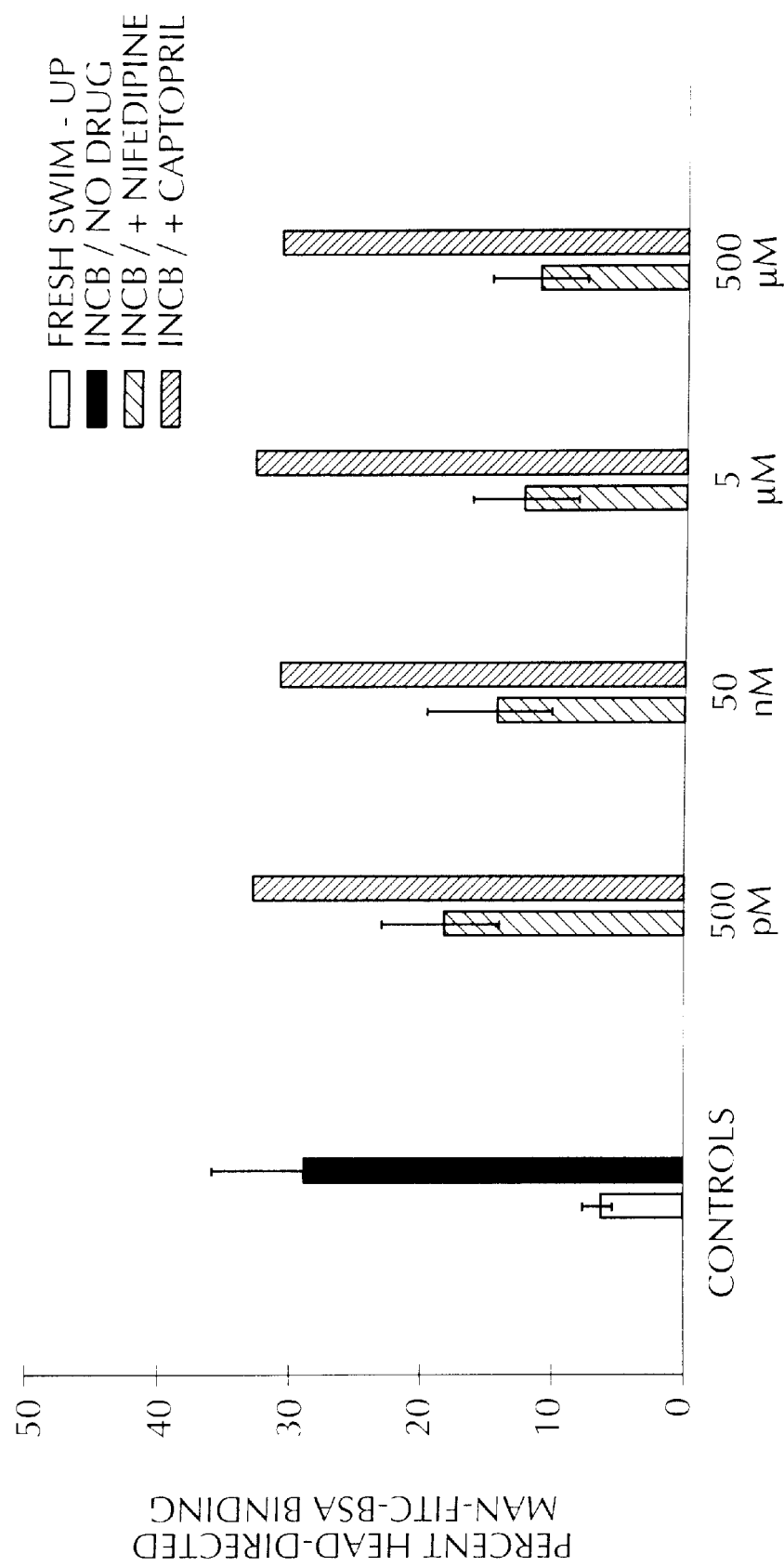

FIG. 15 shows a comparison between the percent head-directed mannose lectin binding found for controls, for sperm incubated in vitro in the presence of nifedipine, a calcium channel blocking drug, and in vitro in the presence of captopril, an acetylcholinesterase (ACE) blocking drug.

DETAILED DESCRIPTION OF THE PREFERRED EMBODIMENTS

The objects and advantages described above, and further objects and advantages that will be apparent to those skilled in the art, stem from several discoveries.

A number of these discoveries relate to the processing steps involved in labeling mannose lectins on sperm cells. The first discovery was that the addition of calcium to the reaction medium when sperm cells are labeled with a mannose-label compound improves the specific binding of the label to the sperm cells. The second discovery was that using a wash medium having a substantially lower calcium content decreases the background labeling which otherwise can be problematic. The third discovery was that capacitation in a proteinaceous capacitating medium gives a greater degree of capacitation, and that this increases the distinction between certain labeling patterns.

Some of the other discoveries from which this invention is derived relate to the specific labeling patterns that can be discerned when mannose lectins are labeled on mammalian sperm cells. One such discovery is that three basic patterns are seen, which are illustrated generally in FIG. 2. Another is that when the percentages of cells showing each type of labeling pattern are determined, the levels of pattern II and pattern III are quite substantially higher for fertile sperm cells than for infertile sperm cells. Yet another discovery is that when sperm samples before and after capacitation are compared, the levels of labeling pattern II are substantially different for fertile and infertile cells.

Another important discovery has been the finding that the above-mentioned differences in labeling patterns for fertile and infertile cells are surprisingly statistically significant, and are predictive of fertility or infertility in a way that is of considerable clinical utility. In addition, this finding has led to the additional discovery that this method can be used to determine whether potential or actual drug compounds, or toxins or environmental pollutants, might have an effect on fertility.

It is important to an understanding of the present invention to note that all technical and scientific terms used herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular buffers, media, reagents, mannose lectin labeling reagents, cell quantitation means, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system for another, use a molecule other than BSA as the label carrier, to use a different, even non-fluorescent probe, use a cell counting machine instead of a microscope, etc., such that a different but known way is used to achieve the same goals as those to which the use of a suggested method, material or composition is directed.

It is additionally important to recognize that although the sperm samples described herein were derived from human donors, the diagnostic and analytical aspects of the present invention are not limited to use in humans. It is well within the skill of the artisan to use the described methods and kit to identify and quantitate mannose lectin binding to sperm from other mammalian organisms, or to evaluate sperm fertility. This may be a particularly important and useful aspect of the invention, e.g., to use these methods to study and evaluate semen from cattle, horses, steer, pets, and other animals in which breeding is of interest.

Finally, it is important to note that the present invention is not limited to the use of all of the specified discoveries together. Although combining these discoveries may indeed be preferred, it is not necessary to the invention that all aspects be used simultaneously. For example, it is possible to use the labeling procedure and examine cells for the noted labeling patterns, yet not provide the cells with the opportunity to capacitate.

In one embodiment of the invention, a method for determining the distribution of mannose lectins on mammalian sperm cells is provided, wherein the sperm cells are reacted with a detectable carrier to which one or more mannose moieties have been bound, and such reaction is carried out in the presence of calcium at a level substantially higher than the physiological level. The sperm cells are then washed with a solution having a calcium concentration substantially lower than that used in the prior step, and are examined to detect the presence and distribution of the detectable carriers on the sperm cells.

As used here, the term "detectable carrier" is intended to mean any molecule or moiety which might be attached to mannose molecule(s) covalently, ionically, by encapsulation, or otherwise, and which can be detected by some means. For example, an enzyme linked assay might be used, wherein mannose could be attached to an enzyme that is detectable with certain reagents. On the other hand, the carrier need not be a protein at all. Furthermore, a radioactive mannose might even be used, in which case the "carrier" would be part of the mannose molecule itself. These examples are not intended to be limiting, and those skilled in the art can easily find a wide variety of ways by which mannose molecules could be rendered detectable, and all of these would be within the scope of this invention, and within the scope of the term "detectable carrier" as used herein.

In stating that calcium levels in the reaction solution should be substantially above physiological levels, "physiological levels" are considered to be about 2.25 to 2.65 millimolar, depending on how the measurements are made (29). Thus, it is intended that the calcium levels in the reaction mixture be above about 2.65 mM by more than a trivial amount. A preferred calcium level in the labeling medium is about 20 millimolar; however, calcium levels from about 2.65 mM to concentrations far in excess of 20 mM, and even 1M or more, would be well within the scope of the present invention, as would each possible concentration inbetween.

In stating that calcium levels in the wash medium should be below physiological levels, it is meant that the calcium concentration should be less than about 2.25 mM. A preferred calcium concentration in the wash medium is zero; however, calcium levels from about 2.25 mM down to zero would be well within the scope of the present invention, as would each possible concentration inbetween.

Examining sperm cells for the presence and location of labeling can be done by a wide variety of means that are well known to those skilled in the art. For example, microscopic examination, examination with the naked eye, detection of radiolabeled compounds or moieties by use of an X-ray film, etc. are all well within the scope of this invention.

In another embodiment of the invention, sperm cells are first incubated under capacitation conditions before the labeling of mannose lectins. Although it is preferred that such capacitation conditions include the presence of a protein such as serum albumin, and although a preferred capacitation medium and other conditions are described herein, it is not intended that the term "capacitating conditions" be limited to these. Those skilled in the art are aware of a variety of media and conditions that can promote or at least allow sperm cell capacitation, and the term "capacitating conditions" is intended to include all such means. This would include even somewhat severe conditions, e.g., incubation for three days at room temperature. Moreover, it is intended that "capacitation conditions" mean any conditions that lead to or at least allow sperm cells to become capacitated, and it is not therefore necessary to the definition of this term that particular conditions even yet be known in order to be included within the scope of the term as used herein.

Several embodiments of the invention include an evaluation step, in which the sperm cell samples are examined to determine the number that show each of the mannose label distribution patterns I, II, and/or III. These label distribution patterns are diagrammed in FIG. 2, and examples of how these patterns actually look under the microscope are shown in FIG. 3. They can be verbally described as follows: Pattern I=midpiece alone; pattern II=whole head plus midpiece; pattern III=equatorial/post-acrosomal regions plus midpiece. However, it is not intended that these patterns be viewed rigidly, as there is considerable variation in the shape and definition of the labeled regions. It is, therefore, intended that those skilled in the art will examine these figures, and then use them as a basis for deciding which cells in a given microscope field can best be said to fall into each class. As those skilled in the art will appreciate, such determinations are somewhat subjective, and different observers may disagree upon which pattern is exhibited by a given cell. This is to be expected, and cell labeling patterns that are not identical to those in the figures are not to be disregarded, but their membership in one of the three classes is to be determined to the best of the observer's ability.

Several embodiments of the invention also call for the quantitation of sperm cells exhibiting certain labeling patterns. For example, in one embodiment it is necessary to determine whether the total percent of sperm cells having label binding pattern II or III is greater than or below about 20%. Although the preferred threshold for distinguishing fertile from infertile sperm is stated to be 20% in this example, it is intended that other percentages might be used as thresholds as well, such as 15%, 20%, 25%, 30%, 35%, 40% and so on, even though the results thus obtained may or may not be as reliable. It is well within an ordinary skill in the art to optimize this parameter in a given setting. In addition, it is within the scope of this invention to use multiple thresholds; for example, it might be desirable to consider all sperm having less than 15% labeling as infertile, and thus poor candidates for IVF, and to consider all sperm having more than 25% as being fertile, and being suitable candidates for IVF. There are a variety of ways in which such thresholds can be manipulated within the scope of the invention, which would be clear to those of skill in the art. The same can be said for the thresholds stated in other embodiments. For example, in one other embodiment, fertility or infertility is determined by measuring whether the total capacitation-induced increase in sperm cells having label binding pattern II was between about 10% and about 80%, which indicates the absence of such infertility, or whether the total capacitation-induced increase in sperm cells having label binding pattern II was less than about 10%, which indicates the presence of such infertility. Again, it is quite possible to successfully use the invention by choosing other thresholds, e.g., 65%, 70%, 75%, 85%, 90%, etc. for the upper one and 2%, 5%, 15%, 20%, etc. for the lower one. Other threshold levels could similarly be chosen for use in other embodiments of the invention. Again, it would also be well within the skill of the ordinary practitioner to determine the optimum threshold and other conditions.

Another embodiment of the invention is a kit for determining the distribution of mannose lectins on mammalian sperm cells, which could also be used as a sperm cell fertility test kit. The components of this kit are not intended to be limited to those described herein, as it is well within the ordinary skill in the art to substitute functionally equivalent components or parts thereof for those described in the preferred embodiments.

In yet another embodiment of the invention, methods of screening for the effects of drug candidates, drugs, toxins, and environmental pollutants on male sperm cell fertility is described. In the descriptions of such embodiments, phrases such as "treating sperm cells with a compound" are not intended to be limited to direct cellular administration. It may mean, for example, administering such compound (intentionally or not) to a mammalian male organism, and then testing to see if the exposure of the organism to that compound has affected sperm fertility. Such administration might be by airborne pollutant inhalation, or by drug delivery means, e.g., administration of pills or injections. Alternatively, such phrases also include the possible direct administration of compounds to sperm cells in vitro, e.g., by adding them to an incubation medium, and then testing to see if there has been an effect.

In one embodiment of the invention, it is suggested that samples might have "inconsistent" lectin binding patterns and acrosomal states. By this it is meant that the acrosomal state is not what one would expect from cells showing the particular mannose lectin labeling pattern that the particular cell has. For example, such an inconsistency would be for cells with labeling pattern III to be acrosomal intact, or for cells with pattern II to be acrosome-reacted. Other such inconsistencies are possible. By "consistent" acrosomal and mannose lectin labeling patterns, it is meant that the acrosomal state is what is expected for cells having the given pattern; for example, cells with pattern III are expected to be acrosome-reacted.

It is important that the meaning of a number of other terms be clearly understood. The term "quantity" as used herein is intended to mean relative quantity and/or absolute quantity, as those terms are commonly understood. In addition, in several instances, the term "mannose lectin-correlated infertility" is used. This phrase is intended only to mean that the mannose lectin labeling patterns are correlated with the infertility, and, it is not intended that this mean that the infertility is caused by the mannose lectin (although this may turn out to be the case in at least some forms of infertility). Finally, it is important to note that when the degree of "head-directed" labeling is discussed in the context of the present invention, this means the sum of cells exhibiting labeling in pattern II and pattern III.

MATERIALS AND METHODS

Media and Chemicals

Ham's F-10 tissue culture medium was obtained from GIBCO Laboratories (Grand Island, N.Y.). Unless otherwise noted, all reagents were purchased from Sigma Chemical Company (St. Louis, Mo.).

IVF Patient Populations

Using standard insemination parameters adjusted by morphology and progression to yield 25,000 motile oval sperm per egg, two populations of normospermic men were identified by in vitro fertilization and are the basis of comparisons between fertile and sub-fertile men. Males 1–7 exhibited "normal fertilization" (IVF+), with >70% of the oocytes retrieved fertilized. Male 8 "failed" two rounds of IVF with, respectively, 1 out of 17 oocytes fertilized and subsequently 1 out of 22 with partial zona dissection (performed elsewhere). For the purposes of statistical considerations, male 8 was grouped with males 9–12 who exhibited complete fertilization failure (IVF−), where no sperm were seen to bind to or penetrate the zona. Note that: [1] males 8–12 would not be classified as "male factor" by the strict priorities advocated for IVF (12), [2] there were no anti-sperm antibodies (13) contributing to the IVF failures, and [3] there were no confounding females factors, e.g., more than 70% of all retrieved oocytes had undergone meiosis and were mature.

Semen Preparation

Fresh semen specimens, collected by masturbation after 2 to 3 days of abstinence, were subjected to routine semen analysis (14). Sperm were then selected for motility by a "swim-up" method as described previously (13). The number of sperm per mL was determined by hemocytometer count after 1:20 dilution in counting fluid containing 4% phenol. Motility in swim-up preparations ranged from 97% to 100% Alternatively, motile populations were obtained from semen frozen in N-tris(hydroxymethyl)methyl-2-aminoethane-sulfonic acid/tris(hydroxymethyl)aminoethane (TEST)-yolk-buffered medium containing glycerol (Irvine Scientific, Santa Ana, Calif.) by Percoll density gradient centrifugation. Three step Percoll gradients, 40%, 70%, and 90% (2:1:2 mL each) were overlaid with semen diluted with Ham's F-10 (1:1, v/v) and spun for 55 minutes at 300×g. Motile sperm were pelleted into 90% Percoll with 80% to 90% motility routinely obtained following three washes in Ham's F-10.

Untreated ("fresh" or uncapacitated) sperm isolated by swim-up or Percoll gradient centrifugation were prepared for analysis by centrifugation (500×g for 8 minutes) to concentrate sperm. To induce capacitation, sperm were pelleted, resuspended in Ham's F-10 containing 30 mg/mL human serum albumin (HSA) at a density of $12 \times 10^6$ cells/mL and incubated for 16 to 20 hours at 37° C. in 5% CO2 in air. At the end of the incubation, sperm were collected by centrifugation and their motility was assessed by phase-contrast microscopy. Only preparations with >80% motile sperm were then used in the experiments reported here.

Solid-phase Sperm Binding Assay

The protocols employed have been modified from those of Bronson et al. (13). Mannosylated polyacrylamide beads (MPBs), 2–5+ microns in diameter (E-Y Laboratories, San Mateo, Calif.), were washed by centrifugation in Dulbecco's phosphate buffered saline (PBS) to remove sodium azide and resuspended in 10 mg/mL ovalbumin (Miles Scientific, Kankakee, Ill.) in PBS by sonication with a Branson sonifier (model 350, Branson Ultrasonics Corp., Danbury, Conn.). For these experiments only, motile sperm populations from one known fertile donor were obtained by swim-up into Biggers, Whitten and Whittingham (BWW) medium containing 5 mg/mL bovine serum albumin (BSA; ICN ImmunoBiologicals, Lisle, Ill.) and used immediately or following overnight incubation at 37° C. in 5% CO2 in air or at room temperature in BWW supplemented with at least 5 mg/mL BSA. Sperm were washed in 5 mg/mL ovalbumin prior to exposure to MPBs. Sperm suspensions (5 to 10 uL) were added to 50 uL of MPBs (at a concentration of 5 to 8 mg of beads per mL) in glass tubes, mixed and then placed on glass slides and covered with 22×22 mm coverslips. MPB binding was observed under phase-contrast microscopy at 200× magnification. Binding was enumerated in two ways: [1] as percent of sperm binding MPBs, a measure of the total number of sperm within a population capable of mannose-ligand binding, and [2] as the per head (head/equatorial region/acrosome) binding number versus binding over the tail (midpiece [MP] or principal piece of the tail [TT]), in order to quantitate potential capacitation-associated differential expression of independent binding domains. Successive sets of 100 motile sperm were counted to eliminate artifacts due to two body interactions; repetitive counting was performed until the variation between sets reached a plateau value of <10%. D-mannose binding specificity was determined by binding percentages in the presence and absence of 20 mM D-mannose or D-galactose.

Visualization of D-mannose Binding Sites

The surface of motile sperm was labeled with neoglycoprotein ligands prepared by reaction of glycosidophenyl-isothioscyanates with BSA (15). Sperm were washed 3 times with core buffer (30 mM HEPES, pH 7.0, 0.5 mM MgCl2, 150 mM NaCl, 10 mg/mL BSA) containing 20 mM [Ca2+] and reacted with 100 ug/mL fluorescein isothiocyanate (FITC)-conjugated mannosylated BSA (Man-FITC-neoglycoprotein ligand; Sigma No. A7790) in calcium-supplemented core buffer for 15 minutes at 37° C. in a humidified environment in 5% $CO_2$ in air. Following labeling, motile sperm were pelleted by centrifugation, washed twice with core buffer (no calcium added), air-dried onto 70% isopropanol cleaned glass slides and mounted in a glycerol-based medium. Specimens were viewed at 400× with an Olympus microscope (Olympus Corp., Lake Success, N.Y.) equipped with epifluorescence optics (BP 490 band pass excitation filter, 500 dichroic filter and LP 515 long pass barrier filter) and photographed on 35 mm/400 ASA black and white film (Eastman Kodak Co., Rochester, N.Y.). Control reactions contained 100 ug/ml FITC-conjugated BSA. Specificity of surface labeling was demonstrated by the inclusion of varying concentrations of the competing sugar, D-(+)-mannose or non-competing sugars (D-galactose, galactosamine, etc.) in the pre-wash and labeling reactions. (Not shown).

Quantitative Analysis of D-mannose Binding Sites

The proportion of spermatozoa showing different topographical patterns of Man-FITC-neoglycoprotein ligand binding was assessed by visual inspection of mounted slides stored at 4° C. for <two weeks prior to analysis. Binding was enumerated as midpiece alone (pattern I) versus whole head plus midpiece (pattern II) versus equatorial/post-acrosomal regions plus midpiece (pattern III). A minimum of two to three independent specimens were evaluated for each fertile and infertile male undergoing IVF treatment. Coded slides from each specimen were examined at 400× by two independent observers, each scoring at least 300 sperm in 10 to 20 microscopic fields. The proportions of sperm displaying patterns II and III Man-FITC-neoglycoprotein binding in swim-up specimens and in liquid nitrogen-frozen/thawed-Percoll gradient purified semen specimens from the same individuals varied by <5% at 0 and at 18 hours irrespective of whether said specimens were obtained from fertile (IVF+) or subfertile (IVF−) males, indicating that storage had no detectable effect on the mannose ligand-binding characteristics of sperm populations (not shown).

Acrosome Status Evaluation

Acrosome-intact and acrosome-reacted Man-FITC-neoglycoprotein ligand labeled sperm were ethanol permeabilized and differentiated by reaction with 100 ug/mL rhodamine-labeled Pisum sativum agglutinin (RITC-PSA; Vector Laboratories, Inc., Burlingame, Calif.) in distilled water as described by Cross et al. (16). Specimens were then mounted and viewed at 400× (using a filter combination specific for rhodamine [BP 545 excitation, 580 dichroic filter and LP 590 barrier], with EY455 supplemental excitation and G520 supplementary barrier filters to prevent secondary RITC label from overpowering the primary FITC label). Sperm were scored as [1] acrosome-intact if the anterior and equatorial regions of the head were uniformly RITC-PSA labeled, or as [2] acrosome-reacted if only the equatorial segment was labeled or if sperm heads were completely RITC-PSA negative. At least 300 sperm in a minimum of 20 microscopic fields were scored for Man-FITC-neoglycoprotein binding and acrosomal status by successive adjustments of the barrier and excitation filters.

Comparison of the fraction of acrosome-intact and acrosome-reacted sperm in specimens of Man-FITC-neoglycoprotein/ RITC-PSA double-labeled sperm with that in duplicate aliquots labeled with RITC-PSA alone, both before and after incubation in capacitating medium, indicated that prior Man-FITC-neoglycoprotein surface labeling had no discernable effect on the assessment of acrosomal status (not shown).

Statistical Analysis

All statistical analyses were performed on an IBM/PS2 computer with the SAS PC software package (SAS-Institute, Inc., Cary, N.C.). Student's t Test for paired comparisons (17) was used to determine if a difference exists between fertile and infertile males based on the increment change in mannose ligand binding during capacitation. Coefficients of variation (CV; 17) were calculated to examine the intra-individual variability over time of mannose receptor expression following incubation in capacitating medium.

EXAMPLE 1

Binding of Mannosylated Polyacrylamide Beads

Solid-phase mannosylated polyacrylamide bead (MPB) sperm binding studies were employed to determine the extent of mannose ligand-binding capacity of sperm populations from one fertile donor before and after incubation in capacitating medium (FIG. 1). Observed under phase-contrast optics, his freshly isolated sperm have only low affinities for MPBs over both the head and tail surfaces, with fewer than 5% showing stable MPB binding over the head. In contrast, 30% to 40% of sperm from populations incubated at room temperature (RT) or at 37° C. in media supplemented with at least 5 mg/mL BSA exhibited high-affinity head-directed MPB binding.

The sugar specificity of MPB binding was defined by co-incubation of beads and sperm in the presence of 20 mM D-mannose or D-galactose. Only D-mannose quenched MPB binding to background binding of 2% to 8% head-directed binding similar to that seen for freshly isolated sperm and those incubated in BWW alone or in low albumin media (non-capacitating conditions).

EXAMPLE 2

Visualization of D-Mannose Binding Sites

To extend the observations of Example 1, the location of D-mannose binding domains on the surface of motile untreated and incubated sperm was mapped to determine both the mannose ligand-binding characteristics of individual spermatozoa and whether the pattern of surface expression of D-mannose binding sites changes during the course of capacitation. Over 150 separate specimens have been examined after exposure to a mannose-containing, fluorescein isothiocyanate-conjugated neoglycoprotein ligand (Man-FITC-neoglycoprotein) and then to rhodamine-labeled Pisum sativum lectin (RITC-PSA) to establish acrosomal status. Typical results are presented in FIG. 2–4. These have been obtained by analysis of sperm from donors: the fertile male studied by MPB binding and six others with normal semen parameters (>20×106 sperm/mL, >40% motility and at least 50% normal oval head forms with 50% or more of the head covered by the acrosome), chosen from men presenting semen for routine semen analysis.

Figure 2:
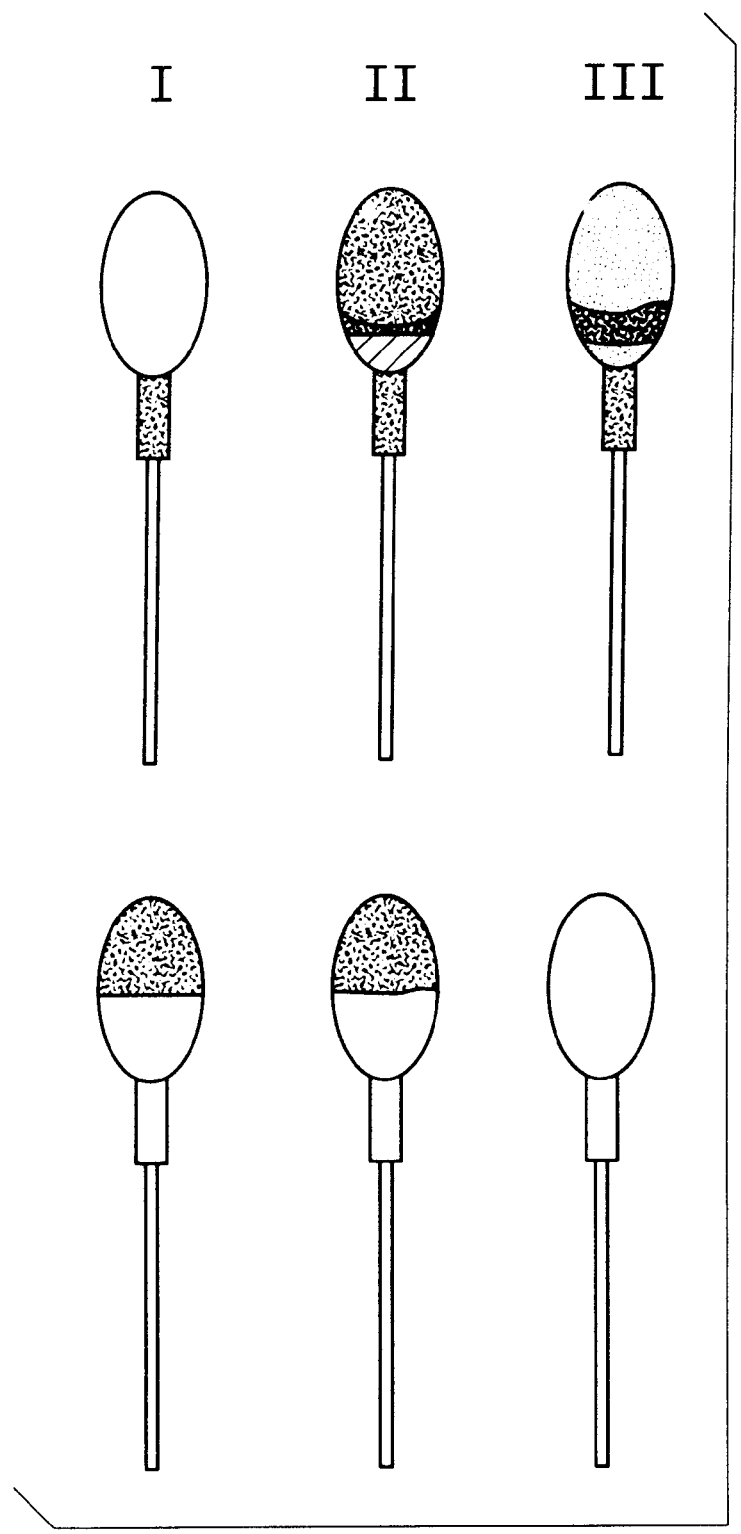
FIG. 2 (upper) shows fluorescence patterns found on sperm after mannose lectins have been labeled with FITC-labeled mannosylated BSA, showing three distinct patterns, identified as I, II and III; (lower) and the patterns obtained when the same sperm are labeled with an acrosome-specific label, RITC-PSA. Sperm exhibiting mannose lectin labeling patterns I and II are acrosome intact. Sperm displaying lectin labeling pattern III have undergone an acrosomal exocytosis. (See FIG. 3 for corresponding photomicrographs.)
Figure 3A:
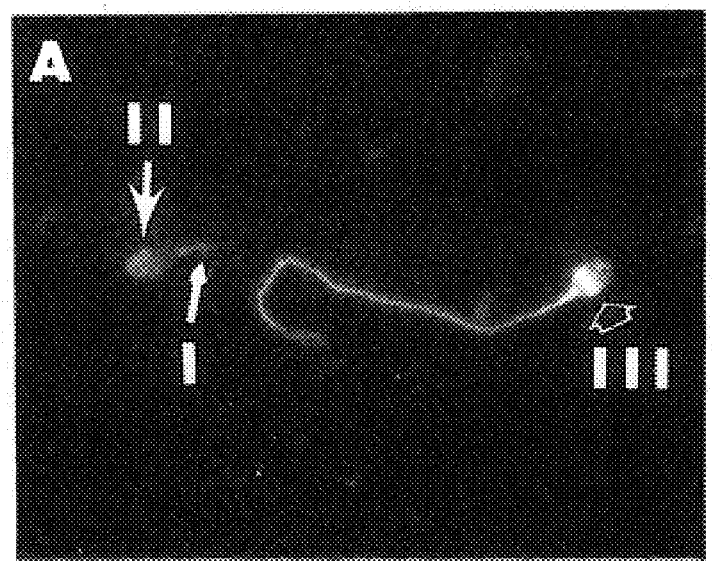
FIG. 3 shows photomicrographs taken with epifluorescent illumination of capacitated human sperm double labeled with Man-FITC-neoglycoprotein ligand and RITC-PSA.
Figure 3B:
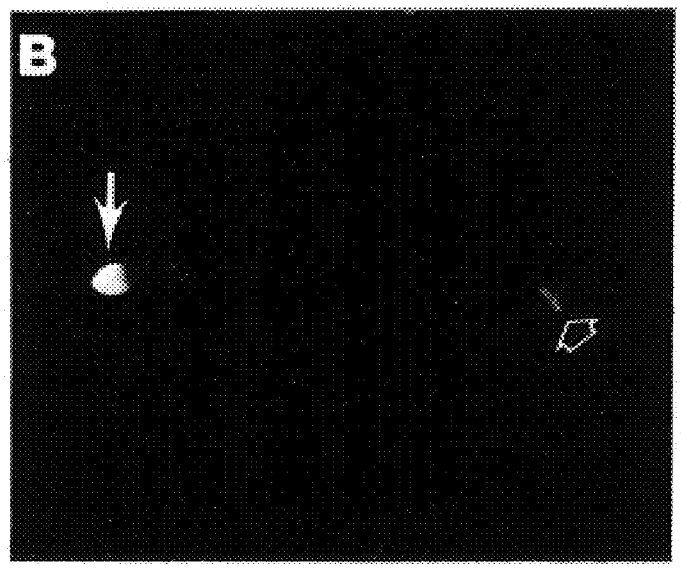

Three characteristic binding patterns are seen, both in untreated specimens and in those incubated at 37° C. for 1 to 18 hours or for 3 days (FIGS. 1–3). All human sperm exhibit non-specific labeling in the neck/midpiece region. In many sperm, only this region was labeled (pattern I). In others, D-mannose binding sites are uniformly distributed over the acrosome and post-acrosomal regions with different intensities (pattern II). Double labeling with RITC-PSA confirmed that these sperm are acrosome intact. After acrosomal exocytosis had occurred, as shown by diminished RITC-PSA labeling, D-mannose ligand-binding sites are visualized on the sperm surface clustered in the equatorial segment and post-acrosomal regions of the head (pattern III). While the percent of sperm exhibiting head-directed surface labeling (patterns II and III) in fresh specimens was consistently low (<9%), this cell population dramatically increased in a time dependent manner plateauing to values >22% by 18 hours (FIG. 3). Nevertheless, the fluorescence intensity characteristic of a cell labeled in pattern II or in pattern III was the same whether the sperm were labeled immediately after swim-up or after incubation in capacitating medium, i.e., cells are either positive or negative for binding.

Surface expression of mannose-specific, head-directed binding sites was observed to increase from <1% to 9% in fresh swim-up specimens from fertile donors (including IVF+ males) to between 20% to 80% in duplicate aliquots exposed to capacitating conditions. Both the time course and the final percent increase varied among semen donors in a fashion consistent with known inter-individual variation in the rate of sperm capacitation (24). D-mannose binding sites were detected over the head surface of fewer than 20% of sperm from IVF− males. Further analysis of D-mannose ligand binding before and after an 18-hour incubation indicates that it is both the total percent of head-directed Man-FITC-neoglycoprotein ligand binding and the differential percent increase in Pattern II binding which distinguish fertile from infertile sperm populations.

Observed differences in sperm head-directed mannose-specific receptor expression between fertile and infertile males can not be attributed to the semen storage or purification protocols. Similar results were obtained with fresh-swim-up and liquid nitrogen frozen/thawed-Percoll gradient purified semen specimens. Finally, comparison of the coefficient of variation (CV), 0.0952, for capacitation-associated surface expression of D-mannose ligand binding sites with CVs for sperm concentration, total sperm number, motility, progression and morphology reported, respectively, as being 0.46, 0.58 to 0.80, 0.27 to 0.36 (range 0.06 to 0.49), 0.19 to 0.20 (range 0.02 to 0.49), and 0.15 (reviewed in Refs. 20 and 21) indicates that Man-FITC-neoglycoprotein binding displays less variation over time than other semen parameters previously studied. Such a comparison of biological variation emphasizes the usefulness of quantitative measurements of D-mannose ligand binding as a marker for reproductive potential.

The sub-fertile men were selected from IVF fertilization failures. Only nine of 292 males (3.1%) undergoing IVF in my program have failed to fertilize eggs in 349 cycles with egg retrieval over the years 1989 to 1991. Three of these 9 cases were in men with severe impairment in sperm parameters where fertilization failure was not unexpected and where the addition of large numbers of sperm to eggs was unable to overcome sperm defects. The remaining 6 failures occurred with men having normal semen parameters and as such were unexpected failures. In the five of these six cases in which fresh and/or frozen semen samples were available for this study, mannose receptor expression was reduced or altered. These males represent 2.1% of my IVF patient population. Samples from these patients were analyzed after 18 hours treatment in capacitating medium. Time course studies of fertile males indicate that the percent of sperm exhibiting head-directed surface expression of mannose ligand-binding sites does not increase any further after this time. However, in samples from these IVF− males, the percent of sperm expressing the mannose-specific receptor may continue to increase with prolonged incubation for at least 3 days (Benoff S, Hurley I, unpublished observations). Clearly, a standard common time of incubation is necessary for meaningful distinctions between fertile and infertile sperm populations.

My studies provide direct evidence for the presence of mannose-specific receptors on the surface of human sperm subjected to capacitating procedures and their reduced expression on the sperm surface in males failing to fertilize oocytes during IVF. Two different patterns of D-mannose ligand binding were identified, both associated with capacitation and which correlate with the ability of human sperm to recognize and fertilize eggs in vitro. D-mannose ligand-binding sites are putative sperm determinants of human oocyte recognition and fertilization.

EXAMPLE 3

Reduced Expression of D-mannose Binding Sites Associated with Unexplained Male Infertility A retrospective double blind analysis of liquid nitrogen stored semen from males participating in my IVF program was undertaken to determine whether the level or topographical arrangement of D-mannose binding sites was altered in morphologically "normal" sperm from infertile men. Specimens from fertile (IVF+) and infertile (IVF−) males with normal semen parameters (i.e., at least 35% normal oval forms) were divided and evaluated before and after 18 hour incubation in capacitating medium. Initial observations were confirmed by analysis of a minimum of 2 additional independent swim-up or stored specimens from the same males. Where possible, concurrent analyses of portions of ejaculates used for IVF were also performed. These studies indicate that the size of the increase in percent head-directed Man-FITC-neoglycoprotein binding following overnight incubation in albumin-supplemented medium is an important indicator of zona binding ability in IVF (FIG. 4A).

The IVF− sperm populations studied have been identified by their inability, following standard incubation, to bind to or penetrate the zona during IVF. High intensity pattern II Man-FITC-neoglycoprotein binding is restricted to the plasma membrane overlying the acrosome, the same region over which sperm first establish tight contact with the zona (1). Limitation of comparisons to quantitation of pattern II expression before and after 18 hour incubation more clearly discriminates between fertile and infertile sperm populations (FIG. 4B) than do combined values for patterns II and III (FIG. 4A). By the Student's t Test for paired comparisons (17), a significant difference (P=0.003) in the net increase in sperm capable of pattern II Man-FITC-neoglycoprotein ligand binding upon exposure to capacitating conditions was detected between the fertile and infertile groups. The magnitude of this difference can best be viewed by comparing the mean percent positive for the fertile group, 42.2%, where almost half of all incubated sperm exhibit pattern II binding, with the mean percent positive for the infertile group, where a mere 1.5% of the sperm exhibit pattern II binding. This translates to a binding increment of 0.1 (equivalent to >50% increase over the untreated state) with a final value of >20% of all sperm displaying head-directed Man-FITC-neoglycoprotein binding associated with successful fertilization of human oocytes in vitro.

EXAMPLE 4

Intra-individual Variation in Mannose-ligand Receptor Expression

Potential variability in capacitation-associated mannose-ligand receptor expression between independent ejaculates from the same male was evaluated. The coefficient of variation (CV), based on the arc sin square root of the proportion of capacitated sperm displaying head-directed Man-FITC-neoglycoprotein binding, was examined for a subset of the IVF+ and IVF− males described above. For the nine males on which it was possible to accrue longitudinal data over an eight month period, the CV ranged from 0.0117 to 0.1499, with a median of 0.0952 and an interquartile range from 0.0802 to 0.1051. This CV is indicative of a small intramale variation over time.

EXAMPLE 5

Mannose Lectin Expression as an Indicator of Fertility Effects of Exposure to Toxic Metals Sperm samples from fertile donors were divided into multiple aliquots and assayed for motility and mannose lectin expression before and after 18 hours incubation in capacitating media. Indicated levels of toxicants were added to the 18 hour incubation medium, and then rinsed out before surface labeling. The occurence of spontaneous acrosomal reactions was indicated by pattern III labeling, and confirmed by RITC-PSA labeling (data not shown).

Figure 6:
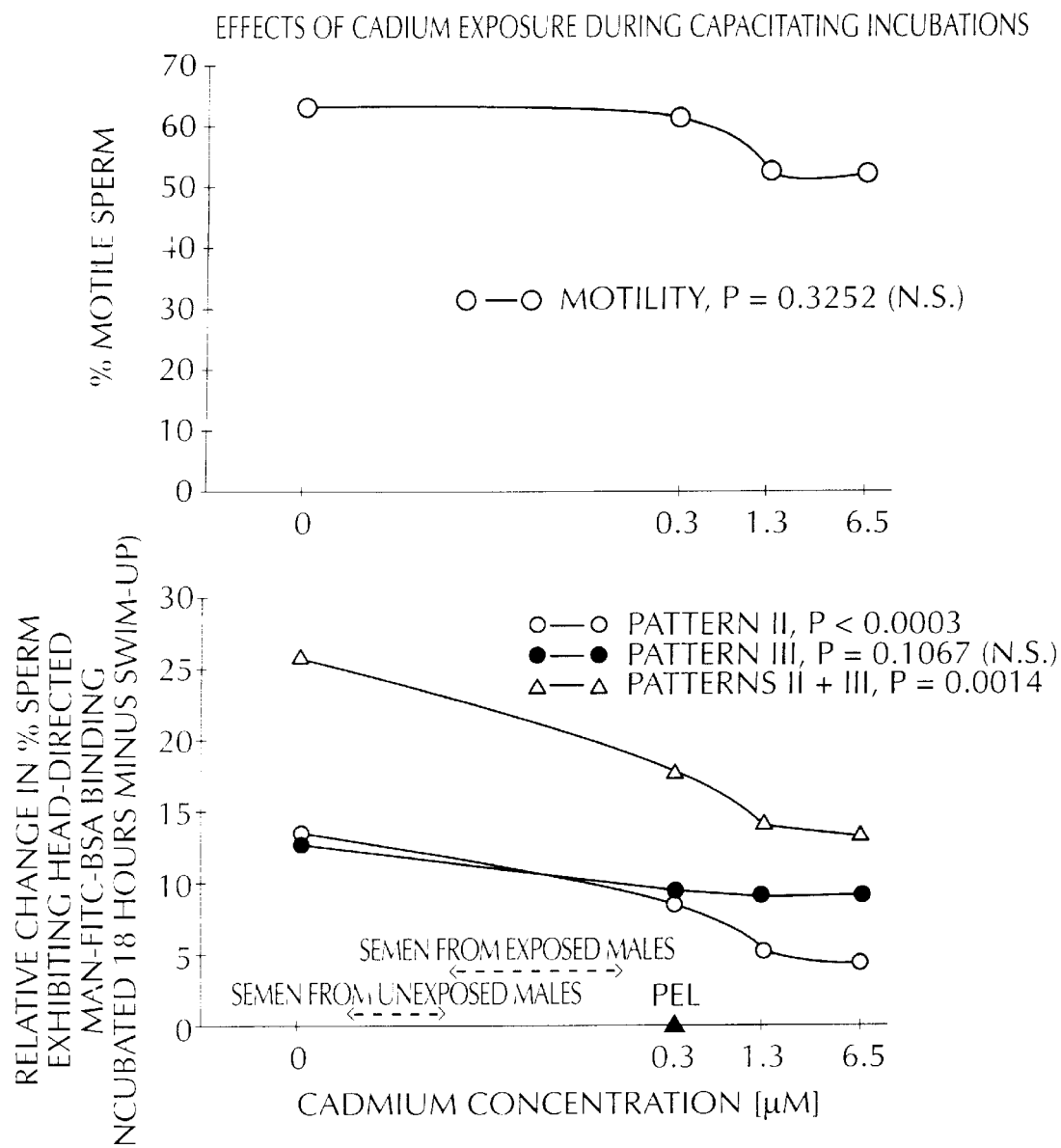
Figure 7:
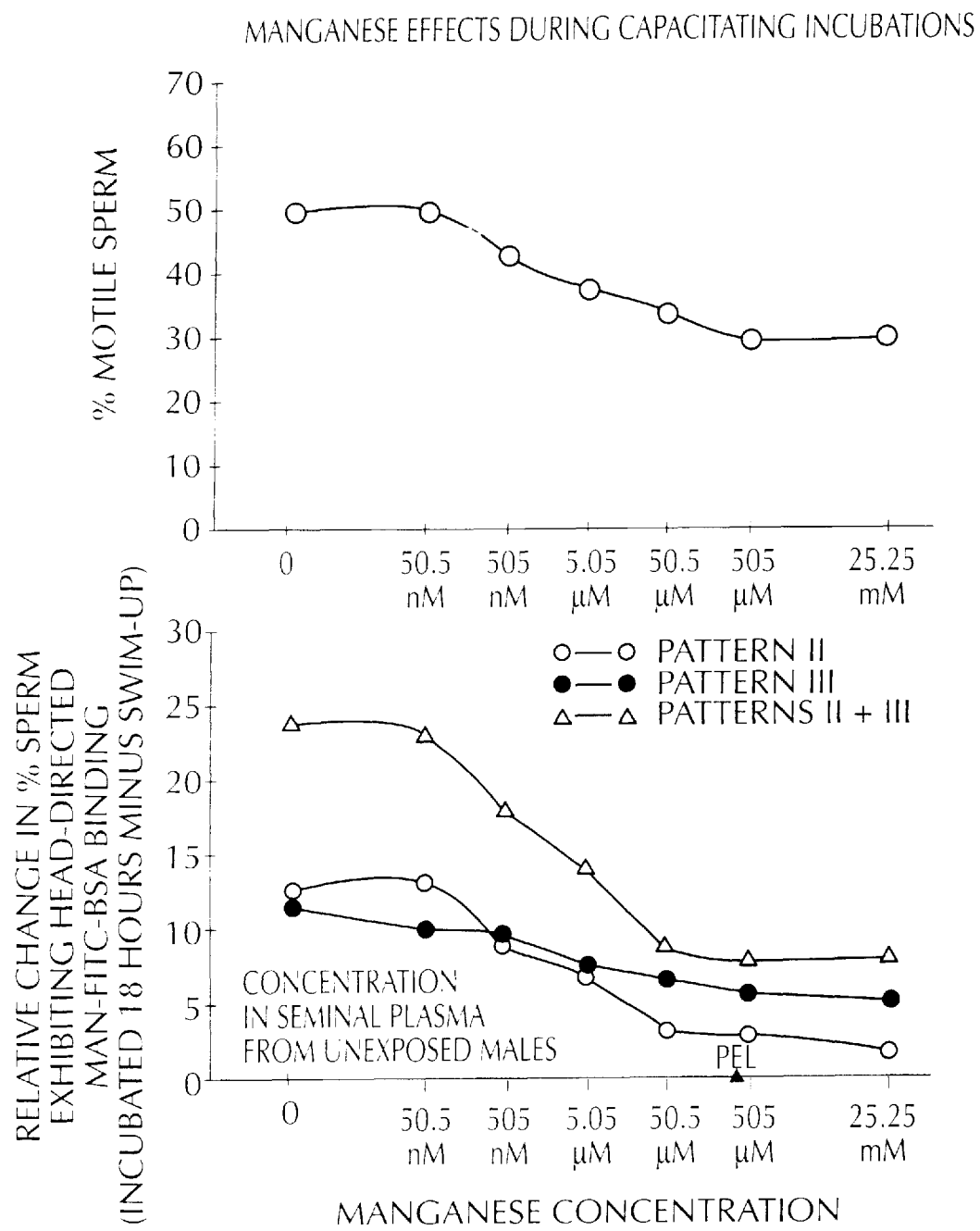
Figure 8:
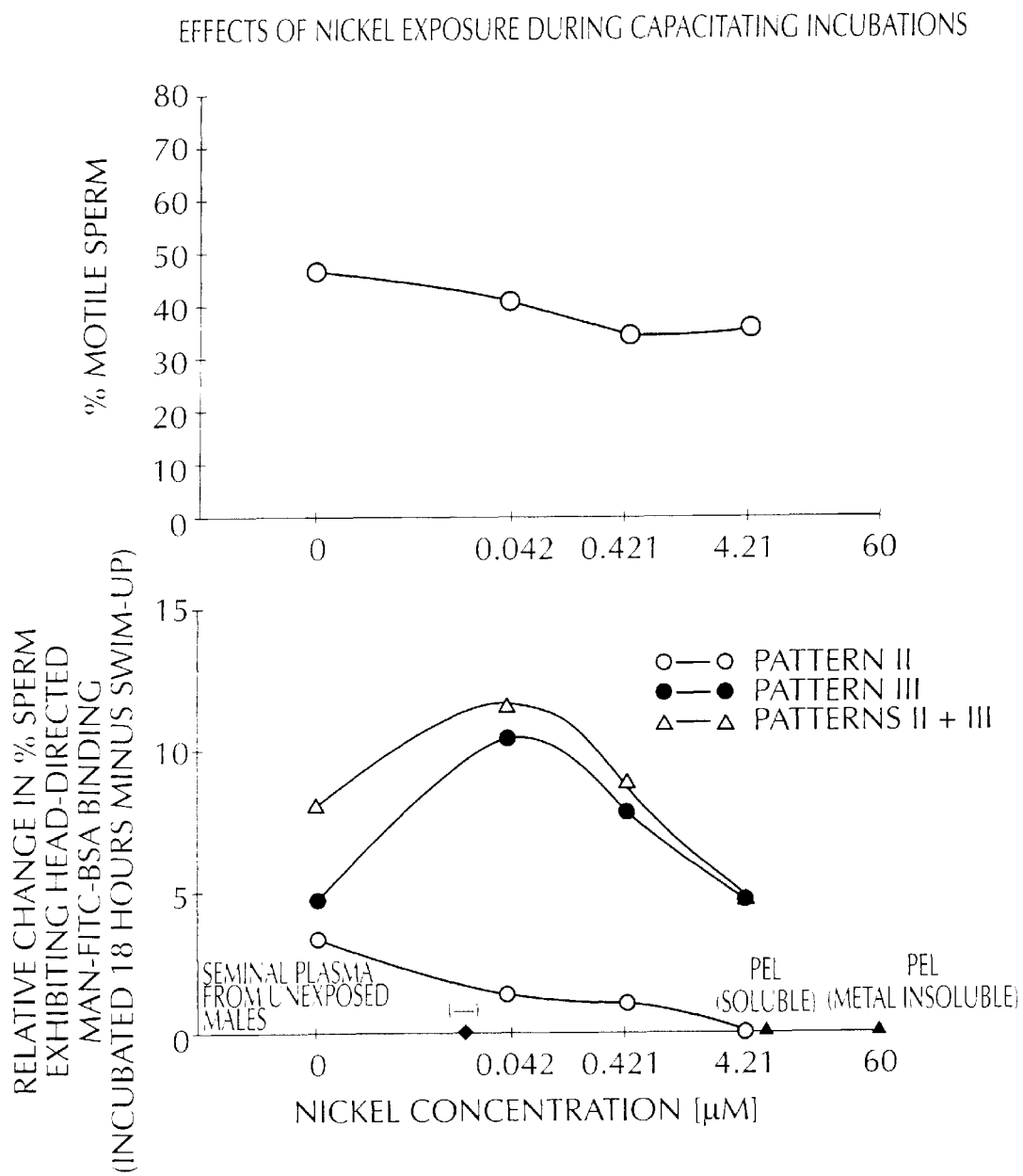

The results are shown in FIG. 6–10. FIG. 6 shows that cadmium, when added in levels found in occupationally exposed males (shown on bottom of lower graph), caused a decrease in the level of functional mannose binding sites, but did not substantially alter the level of spontaneous acrosomal reactions. As shown in FIG. 7, manganese suppresses both mannose ligand binding and spontaneous acrosomal reactions, whereas nickel, as shown in FIG. 8, strongly induces acrosomal reactions at concentrations up to 100 mM, and suppresses acrosome reactions at higher concentrations. Mannose ligand binding is suppressed at all nickel concentrations studied. FIG. 9 shows that zinc has no effect on mannose ligand binding or spontaneous acrosome reactions below levels seen in un-exposed males, but that higher levels of zinc induce acrosomal exocytosis, and mannose ligand binding rises with zinc levels of 100 times normal.

In order to see if metal toxicants affected IVF-infertile non-responders (i.e., those with low intrinsic mannose lectin expression) differently than responders (those with mannose lectin expression within the "fertile" range), experiments similar to those illustrated in FIG. 9 were carried out using sperm from both types of donors. As shown in FIG. 10, relative changes were comparable, indicating that zinc acts on the functionality of surface expressed mannose lectin, rather than on the process of externalization.

EXAMPLE 6

Mannose Lectin Expression as an Indicator of Fertility Effects of Exposure to Organic Toxicants In a manner similar to that used in Example 6, sperm samples from fertile donors were divided into multiple aliquots and assayed for motility and mannose lectin expression before and after 18 hours incubation in capacitating media. Indicated levels of organic toxicants were added to the 18 hour incubation medium, and then rinsed out before surface labeling. The occurence of spontaneous acrosomal reactions was indicated by pattern III labeling, and confirmed by RITC-PSA labeling (data not shown).

The results are shown in FIG. 11–13. FIG. 11 shows that 2,2-dibromoethane decreases both mannose ligand binding and spontaneous acrosome reactions at nanomolar concentrations in sperm from responder males, but has no significant effect from an IVF-infertile male. FIG. 12 shows that phthalate ester affects the percent motile sperm and mannose ligand binding at micromolar concentrations without significantly altering the level of acrosomal exocytosis. FIG. 13 shows that 1,2 dibromo-3-chloropropane decreases the percent motile sperm at micromolar concentrations, but mannose ligand binding and spontaneous acrosomal reactions at concentrations that are two orders of magnitude lower.

EXAMPLE 7

Pharmaceutical (in vivo) Administration of Calcium Channel Blockers is Found to Cause Inconsistent Mannose Lectin Labeling and Acrosomal States A 39-year old male patient with a 7-year history of infertility showed generally normal semen parameter according to the "classical" methods of analysis. Six months prior to the couple's first effort at IVF, this male patient had been treated for hypertension with Procardia (nifedipine, Pratt Pharmaceuticals, Pfizer, New York, N.Y.) at 30 mg/day. Prior efforts at hormonally-stimulated intrauterine insemination had been unsuccessful; IVF was unsuccessful as well.

On the day of the IVF failure, sperm maintained overnight at room temperature in media supplemented with 10% human fertile female donor serum were assayed for mannose lectin labeling. Eight percent of the sperm exhibited head-directed (pattern II and III) mannose lectin labeling, yet only 2.67% of sperm had undergone a spontaneous acrosomal reaction. Importantly, less than 20% of all pattern III labeled sperm had undergone the acrosome reaction, as shown by RITC-PSA labeling. Since virtually all pattern III cells usually appear as acrosome-reacted, the acrosomal status was generally inconsistent with the mannose lectin labeling pattern. Analysis of four additional semen specimens confirmed this finding.

After consultation with the patient's cardiologist, the patient discontinued treatment with Procardia, and was instead treated with an ACE inhibitor, Vasotec, and a diuretic, Dyazide. Semen samples collected after 4 months and 9 months after Procardia therapy was discontinued were indistinguishable from fertile control sperm samples, suggesting that (1) Procardia had caused the inconsistency between the acrosomal status and mannose lectin binding patterns, and (2) that this effect was reversible.

In order to verify these findings, sperm from nine other male patients who were taking calcium channel blockers—Procardia or Verapamil—were tested. These were all found to have surface membrane characteristics that were the same as that of the first case: no time-dependent increases in the percentage of sperm exhibiting head-directed mannose lectin labeling or increases in the occurrence of spontaneous acrosomal reactions were observed, and both pattern II and pattern III mannose lectin labeling occurred on acrosome-intact sperm. Thus, inconsistent acrosomal states and mannose lectin binding patterns were present.

In all nine additional cases, the use of alternate pharmaceutical regimens resulted in a return to normal sperm labeling and acrosomal states.

Figure 14:
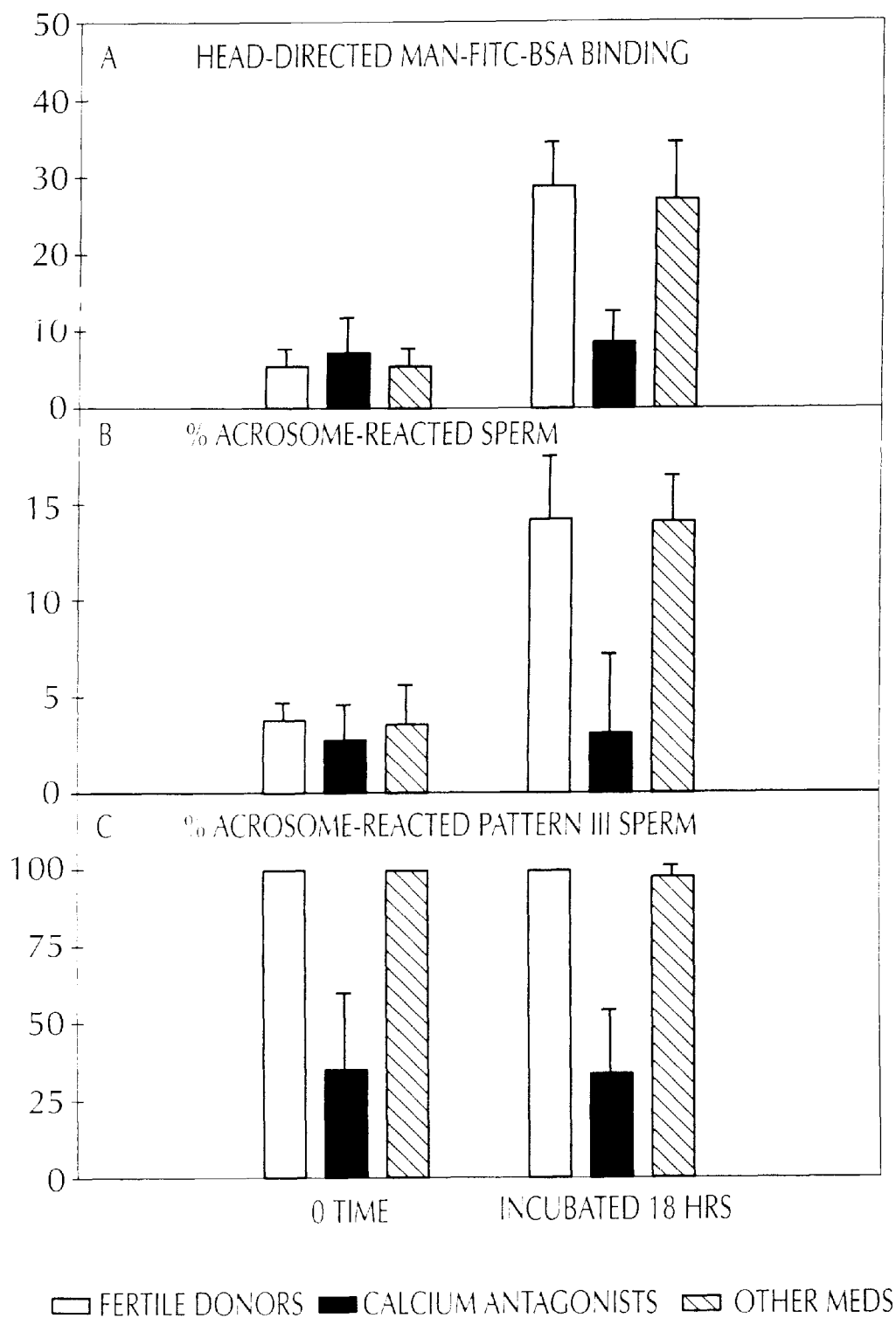

As shown in FIG. 14, patients being treated with calcium channel blockers had far less head-directed mannose lectin labeling after capacitation than did fertile sperm, or sperm from those patients taking other anti-hypertensive medications. Furthermore, patients on calcium channel blockers also had less acrosome-reacted sperm and less acrosome-reacted pattern III sperm than did the other groups.

EXAMPLE 8

In vitro Administration of Calcium Channel Blockers is Also Shown to Cause Inconsistent Mannose Lectin Binding Patterns and Acrosomal States In order to determine if calcium channel blockers exert a dose-response when used to treat sperm cells in vitro, fertile sperm samples were treated with nifedipine (a calcium channel blocker), and additional samples were treated with captopril, an ACE inhibitor. Exposure to the drugs lasted 18 hours, and was carried out in Ham's F-10 medium containing 30 mg/ml BSA at 37° C. As shown in FIG. 15, exposure to nifedipine significantly inhibited capacitation-associated increases in the percentage of sperm cells exhibiting mannose lectin labeling. However, captopril-treated sperm cells appeared to be identical to the control samples.

REFERENCES

Yanagimachi R. Mammalian fertilization. In: Knobil E, Neill J, Ewing L. L., Greenwald G. S., Markert C. L., Pfaff D. W., editors. The physiology of reproduction. New York: Raven Press, 1988:135–85.

Macek M. B., Shur B. D. Protein-carbohydrate complementarity in mammalian gamete recognition. Gamete Res 1988;20:93–109.

Leyton L, Saling P. Evidence that aggregation of mouse sperm receptors by ZP3 triggers the acrosome reaction. J. Cell Biol. 1989;108:2163–8.

Beebe S. J., Leyton L., Burks D., Ishikawa M., Fuerst T., Dean J., Saling P. Recombinant mouse ZP3 inhibits sperm binding and induces the acrosome reaction. Devel. Biol. 1992;151:48–54.

Singer S. L., Lambert H., Overstreet J. W., Hanson F. W., Yanagimachi R. The kinetics of human sperm binding to the human zona pellucida and zona-free hamster oocyte in vitro. Gamete Res. 1985;12:29–39.

Cross N. L., Morales P., Overstreet J. W., Hanson F. W. Induction of acrosome reactions by the human zona pellucida. Biol. Reprod. 1988;38:235–44.

Tesarik J., Mendoza C., Carreras A. Expression of D-mannose binding sites on human spermatozoa: comparision of fertile donors and infertile patients. Fertil. Steril. 1991;56:113–18.

Aitken R. J. Evaluation of human sperm function. Br. Med. Bull. 1990;46:654–74.

Tesarik J., Testart J. Human sperm-egg interactions and their disorders: implications in the management of infertility. Hum. Reprod. 1989;4:729"41.

Mori K., Daitoh T., Irahara M., Kamada M., Aono T. Significance of D-mannose as a sperm receptor site on the zona pellucida in human fertilization. Am. J. Obstet. Gynecol. 1989;161:207–11.

Oehninger S., Acosta A. A., Kruger T., Veeck L. L., Flood J., Jones H. W. Jr. Failure of fertilization in in vitro fertilization: the "occult" male factor. J. In Vitro Fert. Embryo Transf. 1988;5:181–7.

Kruger T. T., Acosta A. A., Simmons K. F., Swanson R. J., Matta J. F., Oehninger S. Predictive value of abnormal sperm morphology in in vitro fertilization. Fertil. Steril. 1988;49:112–17.

Bronson R. A., Cooper G. W., Rosenfeld D. L. Correlation between regional specificity of antisperm antibodies to the spermatozoan surface and complement correlated sperm immobilization. Am. J. Reprod. Immunol. 1982;2:222–4.

World Health Organization. WHO laboratory manual for the examination of human semen and semen-cervial mucus interaction. Cambridge: Cambridge University Press, 1987.

Monsigny M., Roche A. C., Midoux P. Uptake of neoglycoproteins via a membrane lectin(s) of L1210 cells evidenced by quantitative flow cytofluorometry and drug targeting. Biol Cell 1984;51:187–96.

Cross N. L., Morales P., Overstreet J. W. and Hanson F. W. Two simple methods for detecting acrosome-reacted human sperm. Gamete Res. 1986;15:213–26.

Zar, J. H. Biostatistical analysis, 2nd ed. Englewood Cliffs: Prentice-Hall, 1984.

Freund M. Standards for rating the morphology of human sperm: a cooperative study. Int J Fertil 1966;11:97–180.

Fredricsson B. Morphological evaluation of spermatozoa in different laboratories. Andrologia 1979;11:57–61.

Overstreet J. W. Assessment of disorders of spermatogenesis. Prog. Clin. Biol. Res. 1984;160:275–92.

Working P. K. Male reproductive toxicology: comparison of the human to animal models. Environ. Health Perspect 1988; 77:37–44.

Robertson L., Wolf D. P., Tash J. S. Temporal changes in motility parameters related to acrosomal status: identification and characterization of populations of hyperactivated human sperm. Biol Reprod 1988;39:797–805.

Mortimer D., Curtis E. F., Camenzind A. R., Tanaka S. The spontaneous acrosome reaction of human spermatozoa incubated in vitro. Hum. Reprod. 1989;4:57–62.

Perreault S. D., Rogers B. J. Capacitation pattern of human spermatozoa. Fertil Steril 1982;38:258-60.

Barros C., Jedlicki A., Vigil P. The gamete membrane fusion test to assay the fertilizing ability of human spermatozoa. Hum. Reprod. 1988;3:637–44.

Drobnis, E. Z. Capacitation and the acrosome reaction. In Scialli, A. T. and Zinaman, M. J. (eds.), Reproductive Toxicology and Infertility. 1993. McGraw-Hill, Inc., New York, pp. 77–132.

Silverberg, K. M., Dey, T., Schenken, R. S. D-Mannose in Vitro Binding Predicts In Vitro Fertilization. Abstract #P374, Society for Gynecologic Investigation Annual Meeting, Mar. 31–Apr. 3, 1993.

Silverberg, K. M., Dey, T., Witz, C. A., Schenken, R. S. The Modified D-Mannose in Vitro Binding Assay Predicts Fertilization In Vitro. Abstract #O-118, Annual Meeting of the American Fertility Society, Oct. 11–14, 1993.

Review of Physiological Chemistry, 16th Ed., Harper et al., Lange Medical Publications, p. 584.

I claim:

1. A method for assessing in vitro sperm fertilization capability, the method comprising the steps of:

a) obtaining a sperm test sample;

b) allowing capacitation to occur in the sample;

c) contacting the sample with a labeled-mannose containing probe; and d) assessing the in vitro sperm fertilization capability of the test sample by comparing the mannose binding of the test sample to the mannose binding of sperm with in vitro fertilization capability.

2. The method of claim 1, wherein assessing is by fluorescence, a visual means, colorimetry or radioactive methods.

3. The method of claim 2, wherein fluorescence assessing is with flourescein isothiocyanate (FITC).

4. The method of claim 2, wherein visual means assessing is with a polyacrylamide bead using microscopy.

5. The method of claim 1, wherein said probe is mannose coupled to a detectable carrier.

6. The method of claim 5, wherein said detectable carrier comprises an enzyme.

7. The method of claim 1, wherein said detectable carrier comprises bovine serum albumin (BSA) or a polyacrylamide bead.

8. The method of claim 5, wherein said probe is FITC-labeled mannosylated-BSA.

9. The method of claim 1, wherein said test sample is from a domestic animal or a human.

* * * * *